United States Patent
Moretti et al.

(10) Patent No.: US 11,488,696 B2
(45) Date of Patent: Nov. 1, 2022

(54) METHOD AND SYSTEM TO CREATE AND CUSTOMIZE MEDICAL DATA SHEETS AND REPORTING PAGES

(71) Applicant: Ebit srl, Genoa (IT)

(72) Inventors: Marcello Moretti, Carcare (IT); Pierluca Amodeo, Genoa (IT)

(73) Assignee: Ebit srl, Genoa (IT)

( * ) Notice: Subject to any disclaimer, the term of this patent is extended or adjusted under 35 U.S.C. 154(b) by 326 days.

(21) Appl. No.: 16/802,266

(22) Filed: Feb. 26, 2020

(65) Prior Publication Data
US 2020/0279625 A1 Sep. 3, 2020

(30) Foreign Application Priority Data
Feb. 28, 2019 (EP) .................................... 19159914

(51) Int. Cl.
*G06F 3/0482* (2013.01)
*G16H 10/60* (2018.01)
*G06F 16/22* (2019.01)

(52) U.S. Cl.
CPC .......... *G16H 10/60* (2018.01); *G06F 3/0482* (2013.01); *G06F 16/2228* (2019.01)

(58) Field of Classification Search
CPC ...... G16H 10/60; G16H 15/00; G06F 3/0482; G06F 16/2228
See application file for complete search history.

(56) References Cited

U.S. PATENT DOCUMENTS 8,335,694 B2 * 12/2012 Reiner ................... G16H 15/00
  705/2
8,380,533 B2 * 2/2013 Reicher ................. G16H 15/00
  705/2

(Continued)

OTHER PUBLICATIONS

"Enable and Disable Binding Using Knockout", Anubhav Chaudhary, Nov. 27, 2013, XP055611766, retrieved from the internet on Aug. 8, 2019: URL: https://www.c-sharpcorner.com/UploadFile/cd7c2e/enable-and-disable-binding-using-knockout/.

(Continued)

*Primary Examiner* — Hien L Duong
(74) *Attorney, Agent, or Firm* — Gordon & Jacobson, P.C.

(57) ABSTRACT

A computer-implemented method is provided for creating a customized electronic data sheet (EDS), which involves receiving inputs at a graphical user interface (GUI), and executing program instructions at one or more processors to perform operations that include:
  receiving layout instructions, through the GUI, in connection with a page layout to be rendered on a display in connection with entering and viewing clinical data of an EDS
  building a nested EDS database structure, based on the layout instructions, that includes page objects, panel objects and panel item objects nested within one another, the nested EDS database structure defining a manner in which the GUI renders the page layout on the display
  receiving a rule designation through the GUI
  generating a binding rule, based on the rule designation, that binds clinical data to at least one of the page objects, panel objects or panel item objects, the binding rule designating an operation to be automatically performed based on the clinical data.

(Continued)

Corresponding systems and computer programs are also disclosed.

20 Claims, 17 Drawing Sheets

(56) References Cited

U.S. PATENT DOCUMENTS

| | | | |
|---|---|---|---|
| 10,860,655 B2 * | 12/2020 | Murphey | G06F 16/90335 |
| 11,372,949 B1 * | 6/2022 | Agassi | G16H 15/00 |
| 11,373,739 B2 * | 6/2022 | Ozeran | G16H 50/70 |
| 2007/0168223 A1 * | 7/2007 | Fors | G16H 40/20 |
| | | | 705/2 |
| 2010/0138239 A1 | 6/2010 | Reicher et al. | |
| 2013/0159019 A1 * | 6/2013 | Reicher | G06Q 10/10 |
| | | | 705/2 |
| 2013/0346093 A1 * | 12/2013 | Goodgame | G06F 16/345 |
| | | | 705/2 |
| 2016/0314248 A1 * | 10/2016 | Klocek | G16H 10/60 |
| 2022/0051795 A1 * | 2/2022 | Yui | G16H 70/20 |

OTHER PUBLICATIONS

"Knockout: The "visible" binding", Anonymous, Aug. 23, 2018, XP055611771, retrieved from the internet on Aug. 8, 2019, URL:https://web.archive.org/web/20180823132258/http://knockoutjs.com/documentation/visible-binding.html.

EP Extended Search Report dated Aug. 28, 2019 of Application No. 19 159 914.1.

* cited by examiner

Fig. 3D

METHOD AND SYSTEM TO CREATE AND CUSTOMIZE MEDICAL DATA SHEETS AND REPORTING PAGES

CROSS-REFERENCE TO RELATED APPLICATION(S)

The present application claims priority from EP Appl. No. EP19159914, filed on Feb. 28, 2019, herein incorporated by reference in its entirety.

BACKGROUND

Embodiments herein generally relate to electronic data sheets (EDS) and more particularly to creating customized EDS utilizing a nested EDS database structure.

Medical data sheet management software applications are offered today that are used to collect and organize clinical data and create diagnostic reports to distribute to requesting physicians and patients. Conventional medical data sheet management applications are generally provided with a predetermined number of layouts, where the layouts are implemented by software developers according to typical clinical workflows and physician needs. At least some conventional medical data sheet management applications provide a limited amount of customization through custom pages, where the custom pages are prepared in advance by the software developers.

However, conventional medical data sheet management software is limited in the ability to enable physicians to generate custom data sheets and report pages. In general, conventional medical data sheet management software provides a limited set of configuration and customization options. Often, clinicians do not wish to use the available configuration custom pages and customization options.

Therefore, a need remains for improved systems and methods that address the above noted difficulties, as well as other problems that will become available upon reading the text herein.

BRIEF DESCRIPTION

In accordance with embodiments herein, a system is provided for creating a customized electronic data sheet (EDS), which includes a display and a graphical user interface (GUI) that is displayed on the display and configured to receive inputs. Memory stores program instructions. A processor is configured to execute the program instructions to receive layout instructions, through the GUI, in connection with a page layout to be rendered on the display in connection with entering and viewing clinical data of an EDS. A nested EDS database structure is built based on the layout instructions. The nested EDS database structure includes page objects, panel objects and panel item objects nested within one another and also defines a manner in which the GUI renders the page layout on the display. A rule designation is received through the GUI and generates a binding rule, based on the rule designation, that binds clinical data to at least one of the page objects, panel objects or panel item objects, the binding rule designating an operation to be automatically performed based on the clinical data.

Optionally, the processor may be configured to generate, as the binding rule, at least one of a cross validation operation, a mathematical formula, a visibility and enablement binding decision, conditional formatting or a data filtering operation. The binding rule may represent the cross validation operation. The cross validation operation may require a second data value entered into a second panel field in response to a first data value being entered into a first panel field. The binding rule may represent the visibility and may enable binding decision, in which at least one of a second panel or second panel field are either i) hidden and disenabled or ii) exposed and enabled in response to a first data value being entered into a first panel field. The binding rule may represent a notification constraint that may define a constraint on a select data set, such that the processor may be configured to perform a predefined action based on a change in the clinical data in the select data set.

Optionally, the predefined action may include at least one of validating the clinical data, filtering the clinical data, performing an automatic calculation based on the clinical data or confirming a user interface action based on the clinical data. In response to the change in the clinical data, the predefined action may direct at least one of i) the panel to be hidden or ii) a control rule to enter an error state. The layout instructions may define an arrangement, position, and format of a page, a panel within the page, a panel field within the panel. The processor may be further configured to define a linking rule that creates an association between the panel field and rules. The linking rule may define an action in connection with conditions that occur relative to the panel field. The nested EDS database structure may define a nested page layout that may include a first panel within a first page, a first panel item within the first panel and wherein the first panel item further defines at least one of a second page or second panel that includes a second panel item.

In accordance with embodiments herein, a computer implemented method for creating a customized electronic data sheet (EDS) is provided. The method receives inputs at a graphical user interface (GUI). The method executes program instructions at one or more processors to receive layout instructions, through the GUI, in connection with a page layout to be rendered on a display in connection with entering and viewing clinical data of an EDS. The method builds a nested EDS database structure, based on the layout instructions, that includes page objects, panel objects and panel item objects nested within one another. The nested EDS database structure defines a manner in which the GUI renders the page layout on the display. The method receives a rule designation through the GUI and generates a binding rule, based on the rule designation that binds clinical data to at least one of the page objects, panel objects or panel item objects, the binding rule designating an operation to be automatically performed based on the clinical data.

Optionally, the method may generate, as the binding rule, at least one of a cross validation operation, a mathematical formula, a visibility and enablement binding decision, conditional formatting or a data filtering operation. The binding rule may represent the cross validation operation. The cross validation operation may require a second data value entered into a second panel field in response to a first data value being entered into a first panel field. The binding rule may represent the visibility and may enable binding decision, in which at least one of a second panel or second panel field are either i) hidden and disenabled or ii) exposed and enabled in response to a first data value being entered into a first panel field. The binding rule may represent a notification constraint that may define a constraint on a select data set, such that the processor may be configured to perform a predefined action based on a change in the clinical data in the select data set.

Optionally, the predefined action may include at least one of validating the clinical data, filtering the clinical data, performing an automatic calculation based on the clinical data or confirming a user interface action based on the clinical data. In response to the change in the clinical data, the predefined action may direct at least one of i) the panel to be hidden or ii) a control rule to enter an error state. The layout instructions may define an arrangement, position, and format of a page, a panel within the page, a panel field within the panel. The method may define a linking rule that may create an association between the panel field and rules. The linking rule may define an action in connection with conditions that occur relative to the panel field. The nested EDS database structure may define a nested page layout that may include including a first panel within a first page, a first panel item within the first panel and wherein the first panel item further may define at least one of a second page or second panel that includes a second panel item.

BRIEF DESCRIPTION OF THE DRAWINGS

FIG. 3D illustrates a screenshot of a custom page configuration data structure layout in accordance with embodiments herein.

DETAILED DESCRIPTION

Figure 1:
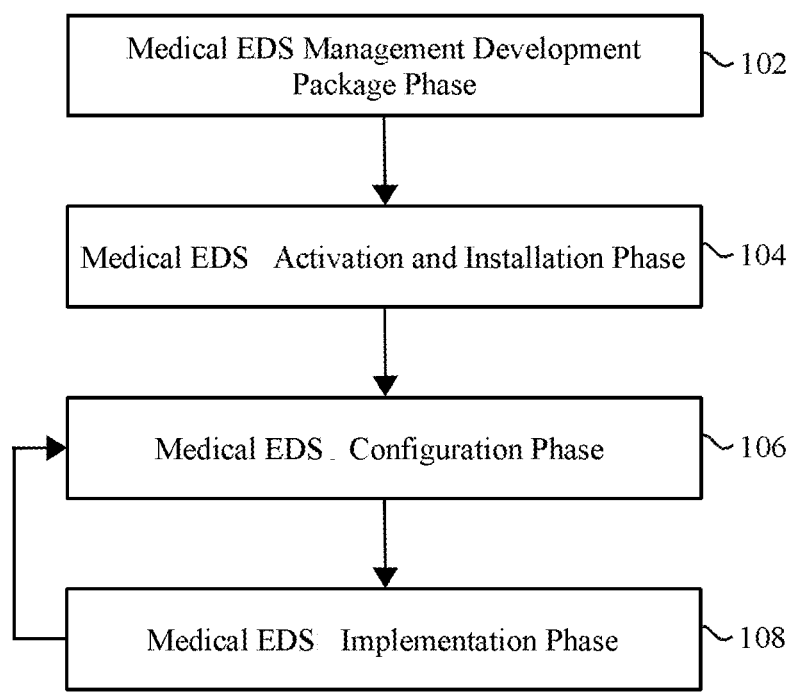
FIG. 1 illustrates a series of phases associated with a medical electronic data sheet management (EDSM) package implemented in accordance with embodiments herein.

The embodiments of the systems and methods described herein may be implemented in hardware or software, or a combination of both. However, preferably, these embodiments are implemented in computer programs executing on programmable computers each comprising at least one processor, a data storage system (including volatile and non-volatile memory and/or storage elements), at least one input device, and at least one output device. For example and without limitation, the programmable computers may be a personal computer, laptop, personal data assistant, and cellular telephone. Program code is applied to input data to perform the functions described herein and generate output information. The output information is applied to one or more output devices, in known fashion.

Each program is preferably implemented in a high level procedural or object oriented programming and/or scripting language to communicate with a computer system. However, the programs can be implemented in assembly or machine language, if desired. In any case, the language may be a compiled or interpreted language. Each such computer program is preferably stored on a storage media or a device readable by a general or special purpose programmable computer, for configuring and operating the computer when the storage media or device is read by the computer to perform the procedures described herein. The system may also be considered to be implemented as a computer-readable storage medium, configured with a computer program, where the storage medium so configured causes a computer to operate in a specific and predefined manner to perform the functions described herein.

Acronyms and Abbreviations

The following (as well as additional) acronyms are used throughout:

The terms "medical personnel", "clinician", "medical user", and similar terms, are used to refer to any individuals or groups who are involved in one or more of examination, diagnosis and treatment of patients, as well as individuals or groups who support and/or take instructions from the foregoing individuals or groups. Non-limiting examples include physicians, nurses, hospital staff, as well as third-party agents and contractors of a hospital or medical facility/network.

The term "panel field" refers to any interactive fields presented within a panel. As nonlimiting examples, a panel field may represent a data entry field, a data output field, an icon designating a hyperlink to other information, and the like. A data entry/output field may contain complex information, such as alphanumeric information, images, tables, graphs, as well as simple information, such as a box that is checked or unchecked, a graphical indicator and the like.

The term "custom page", as used herein, refers to pages or windows displayed on a graphical user interface, where one or more of the content, data fields, format, overall layout and/or linking rules associated with the page or window are directly created by a user (or at a user instruction) after the software has been installed on a server, workstation or other computing device. By way of example, custom pages are not built during the software development phase but instead are created afterwards during a page configuration phase.

The term "rule", as used herein, refers to a constraint on the database resources that may cause an action on the user interface. For example, a constraint on a certain patient dataset may cause an action on the user interface. As a further example, a rule may be a calculation formula. In this case, a certain value may be automatically calculated according to the value of other data. As another example, position of a specific data entry box, or a behavior of a data entry box (e.g., visibility, obligations) depending on the presence or the value of other data may be defined as a rule.

The term "control rule", as used herein, refers to criteria and restrictions that define limits for, and a manner in which, data may be entered, modified or deleted from a database resource. By way of example, control rules may define a manner in which patient data may be edited within a panel item or data field within a clinical database.

The term "binding rule", as used herein, refers to determined criteria and restrictions on data from a database resource depending on values of other data in database resources (e.g., if "patient age" is greater than "16", then hide the "pediatric panel").

The term "nest" or "nested", as used herein, refers to its use in computing science and informatics. For example, nesting is where information is organized in layers, or where objects contain other similar objects. Nesting refers to self-similar or recursive structures in some sense. Nesting is also related to the enclosing of control structures one into another. In this context, "nesting" can mean: i) nested data structures such as records, objects, classes, etc.; and/or ii) nested blocks of control data inside the user interface (e.g., panels inside other panels) with no limits on nesting levels. By way of example, panels, panel items and subpanel items may be nested without limit within one another.

The term "panel item", as used herein, refers to a graphical container (optionally with title) which contains other graphical objects (a set of other panel item grouped in a panel or a set of controls), by way of example, a panel item may contain a panel, other panel items, a list of controls and the like. Nonlimiting examples of types of panel items include a grid panel, a cube panel and a tab panel.

The terms "distributed" and "remote" as used herein in connection with computing devices, computer systems and the like, refers to physical separation (e.g., 1 or more miles) and to separation in ownership/control between two or more different individuals, groups, institutions, companies and/or organizations. For example, the computing devices and computer systems owned and/or controlled by a designer and/or manufacturer of a medical EDSM package are remote from the computing devices and computer systems owned and/or controlled by a medical facility, physician practice group, individual medical personnel and the like.

The following examples represent nonlimiting examples of classes of potential procedures performed and supported by the EDSM package: Peripheral vascular, Abdominal Vascular treatment, Thoracic vascular treatment, Ablation, Angiography, Embolisation, Percutaneous Transluminal Angioplasty (PTA). The following examples represent nonlimiting examples of procedures that may be performed: Supra-aortic vessels district: arteriography, Supra-aortic vessels district: angioplasty, Lower limb district: arteriography, Thoracic district: arteriography, Abdominal district: arteriography, Abdominal district: angioplasty, Aortic-iliac district: arteriography, Aortic-iliac district: angioplasty, Femoral—popliteal district: arteriography, Femoral—popliteal district: angioplasty. The following examples represent nonlimiting examples of angiograms that may be performed: intrathoracic vessel arteriography, Pulmonary artery angiography, Femoral artery angiography, Cerebral arteries angiography, Supra-aortic vessels angiography. The following examples represent nonlimiting examples of arteriography procedures that may be performed: Arteriopathy of supra-aortic vessels, cerebral ischemia: asymptomatic stenosis, cerebral ischemia: isolated TIA (Transient Ischemic Attack), cerebral ischemia: crescendo TIA, cerebral ischemia: recurrent TIA, cerebral ischemia: previous stroke, cerebral ischemia: minor stroke, cerebral ischemia: stroke in progress, cerebral ischemia: major stroke, cerebral ischemia: ocular thromboembolism, Arteriopathy of lower limbs, Arteriopathy of upper limbs.

FIG. 1 illustrates a series of phases associated with a medical electronic data sheet management (EDSM) package implemented in accordance with embodiments herein. The phases may be implemented in a distributed manner at different points in time between multiple computer systems that are located remote from one another.

At 102, one or more processors of a development computer system implement a development phase. During the development phase, medical EDSM package developers construct an overall package architecture that allows subsequent medical personnel (and their agents) to define and config custom pages, panels, panel fields and binding instructions in connection with an individual clinician desire.

By way of example, the EDSM package may be developed with a set of master or base layouts, such as base page layouts and base panel layouts for certain types of examinations and procedures.

At 104, during an activation and installation phase, one or more processors of an implementation computer system load the medical EDSM package to be resident on a local workstation, server or other computing device/network that is managed and/or operated by medical personnel, medical facilities, a medical network and the like. The medical EDSM package is activated, such as by setting up and profiling individual medical personnel accounts, linking the system to third party systems such as patient demographical records, external booking systems, configuring the list and type of examinations that will be reported with the system.

At 106, the one or more processors of the implementation computer system enter a page configuration phase. During the page configuration phase, medical personnel and/or agents thereof step through the operations described herein to define one or more custom pages in connection with an EDS configuration. As part of the definition of the custom pages, the medical personnel and/or agent defines one or more panels within the custom pages, one or more panel fields within the panels and linking rules associated with the panel fields. By way of example, the medical EDSM package presents one or more administration windows where some or all of the available data structures (e.g., page components, panel components, rules to link data) are presented. The administration windows provide an interface to choose and compose different pages, panels, panel fields, etc. according to the individual medical personnel's needs. At the end, the custom page is associated to a specific procedure/examination. That means that when a doctor will want to insert data and write a report of a specific procedure/examination, the preset custom page will be automatically opened.

For example, a medical personnel may want to create an EDS that includes a particular type of medical data, such as correlating patient data of different types (e.g., data coming from previous examinations, data about present clinical conditions, therapies in act, etc.). For example, a cardiologist may desire to correlate 2 different types of patient data with one another (e.g., a check-up visit with an electrophysiology procedure report). Additionally or alternatively, the medical personnel may desire to insert a conditional rule that, when one type of data is entered, the conditional rule directs the EDSM package to open/expose a secondary panel or panel field. The conditional rule may also enable data entry into the secondary panel or panel field based on the type or value of the data entered into the first panel or panel field. For example, when a first panel field is utilized to declare that a patient had previous interventions (i.e. cardiac catheterization), a set of panel fields are enabled, in order to enter details about that intervention.

At least one unique aspect of embodiments herein is that, during the page configuration phase, the methods and systems afford an interface to create nested dynamic panels and panel fields, where the number and structure of the dynamic panels and panel fields are not fixed a prior. For example, a coronary report page may include the information about select lesions and for each lesion, embodiments herein allow medical personnel to config different coronary report pages with different information, such as the lesion characteristics, the imaging method used to identify the legion and the like.

Therefore, during the page configuration phase, the medical personnel are allowed to designate a different set of nested dynamic panel fields for each procedure. There is no limit to the depth of nested data. In addition, during the page configuration phase, the medical personnel are allowed to specify rules that bind clinical data values to designated automatic operations such as crossing validations, formulas, visibility and enable bindings, conditional formatting and data filtering. After configuring the page(s), the medical personnel save the page(s) layout and the included data structures associating the page layouts to a specific procedure type. All the information about the structure of the page is saved and stored inside the system database. Once the configuration phase is complete, flow moves to 108.

At 108, the one or more processors of the implementing computer system enter an implementation phase, during which medical personnel utilize the customize pages in connection with individual patients and specific procedures. Examination/procedure records are generated, populated with data and saved, thereby enriching the patient medical record inside the system. Periodically, throughout operation, it may be desirable to reenter the configuration phase to generate new custom pages (e.g., when there is a desire to report new types of medical visits that need different types of data or rules). Accordingly, the operations of FIG. 1 iteratively loop between the configuration and implementation phases.

During the implementation phase, at for the client-side, when a specific procedure is selected to be reported, all the information about the corresponding page (including its components and their relative position on the display, data formats and validation rules) is collected from the server and rendered at runtime. Since the data and the layouts are stored in separated databases, it is also possible to visualize the inserted data while changing at runtime the layout, by choosing it from the available layouts associated to the same reporting module (see the following section for details about the definition of module).

Figure 2A:
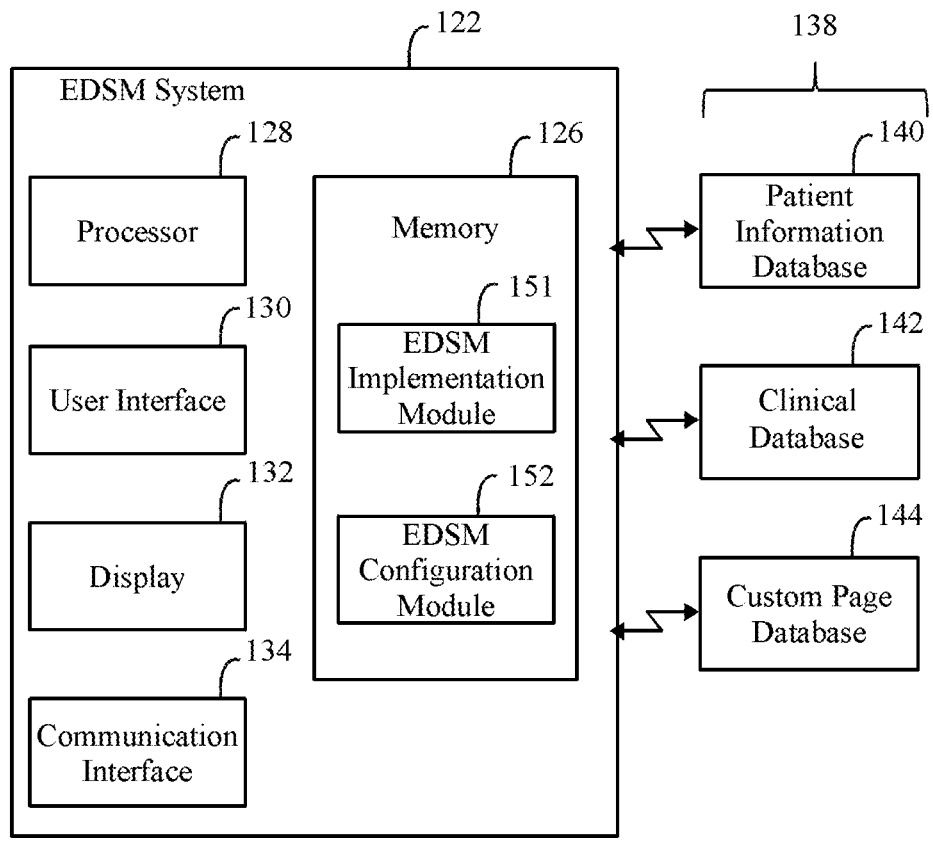
FIG. 2A illustrates an example block diagram of a medical EDSM system formed in accordance with embodiments herein.

FIG. 2A illustrates an example block diagram of a medical EDSM system 122 formed in accordance with embodiments herein. The EDSM system 122 includes one or more memory 126, one or more processors 128, a user interface 130, a display 132 and one or more communications interfaces 134. The memory 126 includes program instructions directing the one or more processors 128 to perform the operations described herein and implemented one or more software modules discussed herein in connection with creating customized electronic data sheets.

The EDSM system 122 communicates with one or more servers having memory 138 that store a patient information database 140, a clinical database 142, and a custom page database 144. The customer page database 144 includes nested EDS structures. Optionally, one or more of the databases 140, 142 and 144 may be located at physically separate locations and/or combined into one database. The patient information database 140 includes patient medical records and other information related to individual patients and their procedure/examinations. The patient information database 140 is practically formed by a pool of examination records that collect data filled with the available custom pages. The clinical database 142 collects all data required to populate the page (e.g., all the clinical information about a specific visit). The patient information database 140 contains personal data of patients (e.g., name, surname, birth date, etc.).

The custom page database 144 includes multiple master or base page layouts that may be associated with corresponding procedures and classes of procedures. For example, each custom page includes one or more panels, each of which may include one or more panel fields, such as data entry fields uniquely associated with particular aspects of a corresponding procedure and report. Additionally or alternatively, the custom page database 144 may include multiple master or base panel layout that may be associated with corresponding pages and/or procedures and classes of procedures. The custom page database 144 collects all data required to build a page (layout, rules, etc.). The custom page database 144 is the database of controls, panels, possible associations rules etc. including the objects that compose a custom page. The custom page database 144 is the set of the reporting pages built (or customized) by composing the objects of the custom page database and associated to the examinations types.

Additionally or alternatively, a report database may be maintained that collects the specific custom pages filled with patient and examination data.

In the example of FIG. 2A, the memory 126 of the servers are described as maintaining the various information as database structures. Optionally, the custom pages, patient medical records and the like may be stored in various formats and upon various medium that may include or not include database structures. The servers and/or memory 138 may be maintained at one or multiple locations, at one or multiple medical facilities, within one or more departments within a medical facility and/or upon one or more pieces of equipment. By way of example, the databases 140, 142, 144 may be distributed across multiple physical locations within a medical network or across multiple medical networks. Optionally, the databases 140, 142, 144 may be maintained upon a single device/workstation or distributed across multiple locations. As one example, a base set of custom pages may be maintained within memory 126 on the EDSM system 122, while additional custom pages may be maintained elsewhere, within or outside of a medical facility or medical network.

The memory 126 may include an EDSM implementation module 151 that is configured to implement the EDSM package. Optionally, the EDSM implementation module 151 may include a quantitative analysis software module that is configured to perform quantitative analysis upon diagnostic images, and other patient data. The EDSM implementation module 151 may also include a mobile/cloud software solution that enables clinical collaboration and results distribution over a wide geographic region and to a variety of end computing devices. The processor 128 provides vendor neutral enterprise archives of patient records and reporting results to enable broad compatibility and interoperability of products and technologies.

The communications interface 134 affords access to external resources, such as medical networks, interventional radiology equipment, medical standards and the like. In accordance with embodiments herein, the data collected may be entered at different times relative to the time in which a procedure occurs. For example, initial information regarding the patient, patient history, past procedures, past prescriptions and the like may be recorded prior to the procedure. Interventional procedure related information may then be entered following the procedure and/or during the procedure.

The memory 126 also includes a medical EDSM configuration module 152 that is configured to manage use of custom pages in connection with building nested EDS database structures for custom pages. The EDSM configuration module 152 further implements the EDS database structures to render the custom page layout during clinical data entry, viewing and report generation. As explained herein, the medical EDSM configuration module 152 builds custom pages that are stored in the custom page database 144. The custom page database 144 maintains various information about each custom page, such as the page layout (e.g., how the page is to be rendered when displayed), configuration information about clinical database structures and rules which describe how to associate clinical data to the layout. The rules may also represent binding instructions and/or constraints between the clinical data and the page layout.

Figure 2B:
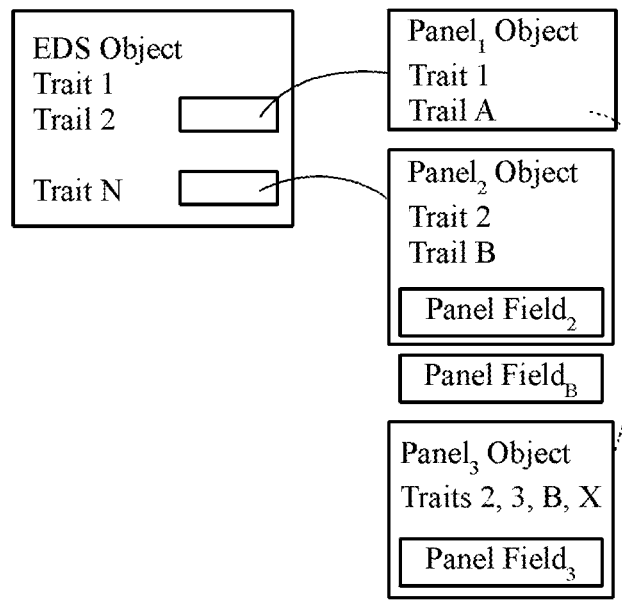
FIG. 2B illustrates an example of a nested EDS database structure formed in accordance with embodiments herein.

FIG. 2B illustrates an example of a nested EDS database structure formed in accordance with embodiments herein. The nested EDS database structure includes one or more main or root EDS objects that define corresponding main or root page(s). The root EDS object includes traits (e.g., traits 1-N) and other information necessary for a computer system to render the root page on a display. Examples of traits for a root EDS object includes tab panel (each label in tab panel layout correspond to a panel item which contains one panel object or data fields) or cube/grid panel object (traits described by rows and columns. The nested EDS database structure further includes one or more panel objects that define corresponding panels that are presented on the root page. The panel objects also include traits and other information necessary for a computer system to render the panel on the display. Examples of traits for a panel object is recursively (nesting) the same at root object: tab panel (each label in tab panel layout correspond to a panel item which contains one panel object or data fields) or cube/grid panel object (traits described by rows and columns). Next, examples are provided for potential page layouts that may be defined as custom pages. It is recognized that the following discussion merely represents non-limiting examples of a manner in which page layouts may be defined for how data may be rendered and presented to a user.

Figure 3A:
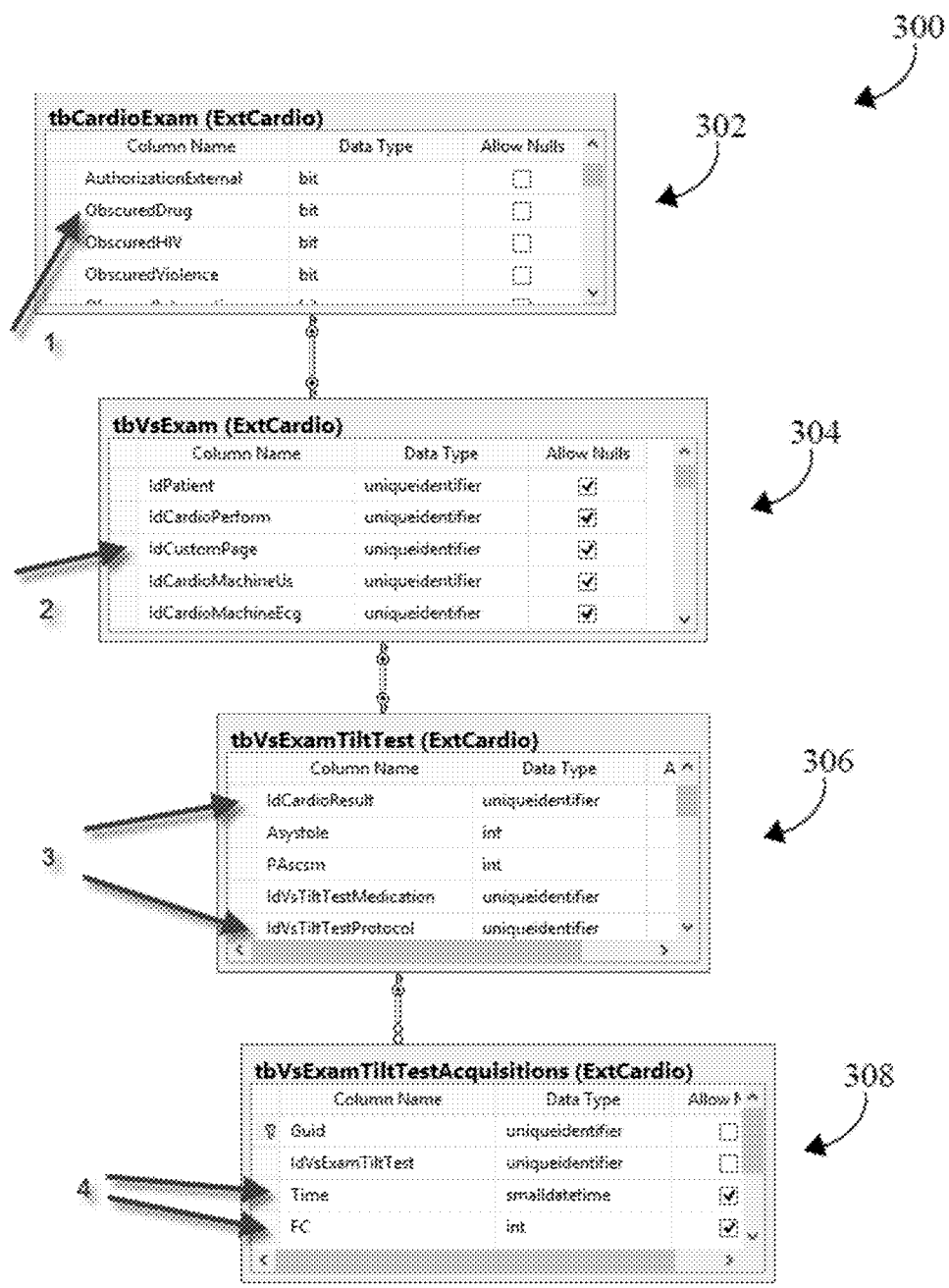
FIG. 3A illustrates examples of data structures that are created in connection with components that are defined within a custom page layout in accordance with embodiments herein.

FIG. 3A illustrates examples of data structures that are created in connection with components that are defined within a custom page layout in accordance with embodiments herein. By way of example, the clinical data structure may be maintained in a clinical database, such as corresponding to the clinical data database 142 in FIG. 2A. The clinical data structure 300 shows a four level data structure. The meaning of this example (300) is that during a visit for a cardio exam, patient can do more tilt test (more instance of 306). A single tilt test can have more data acquisitions (more instance of 308). Every row in 300 represents a data field. Every data field can be also binding source. The data structure 302 includes, by way of example, a data field referred to as "obscured drug". As an example, "obscured drug" can be used as binding source is utilized to manipulate the behavior of data associated with the data field "obscured notes". For example, certain data fields (e.g., a notes field) may be hidden/obscured when a report is generated from an EDS in connection with patients that may experience a drug addiction. It may be desirable to hide certain data fields within reports based on various regulations and to maintain highly sensitive patient information as confidential. The layout identifiers 304 are utilized in connection with opening a preferred, custom page layout. In the present example, the layout identifier "ID custom page" is designated. The data fields 306, 308 are included within the custom page "ID custom page". The data fields 302, 306, 308 are configured to be edited at various levels within a series of nested pages.

Figure 3B:
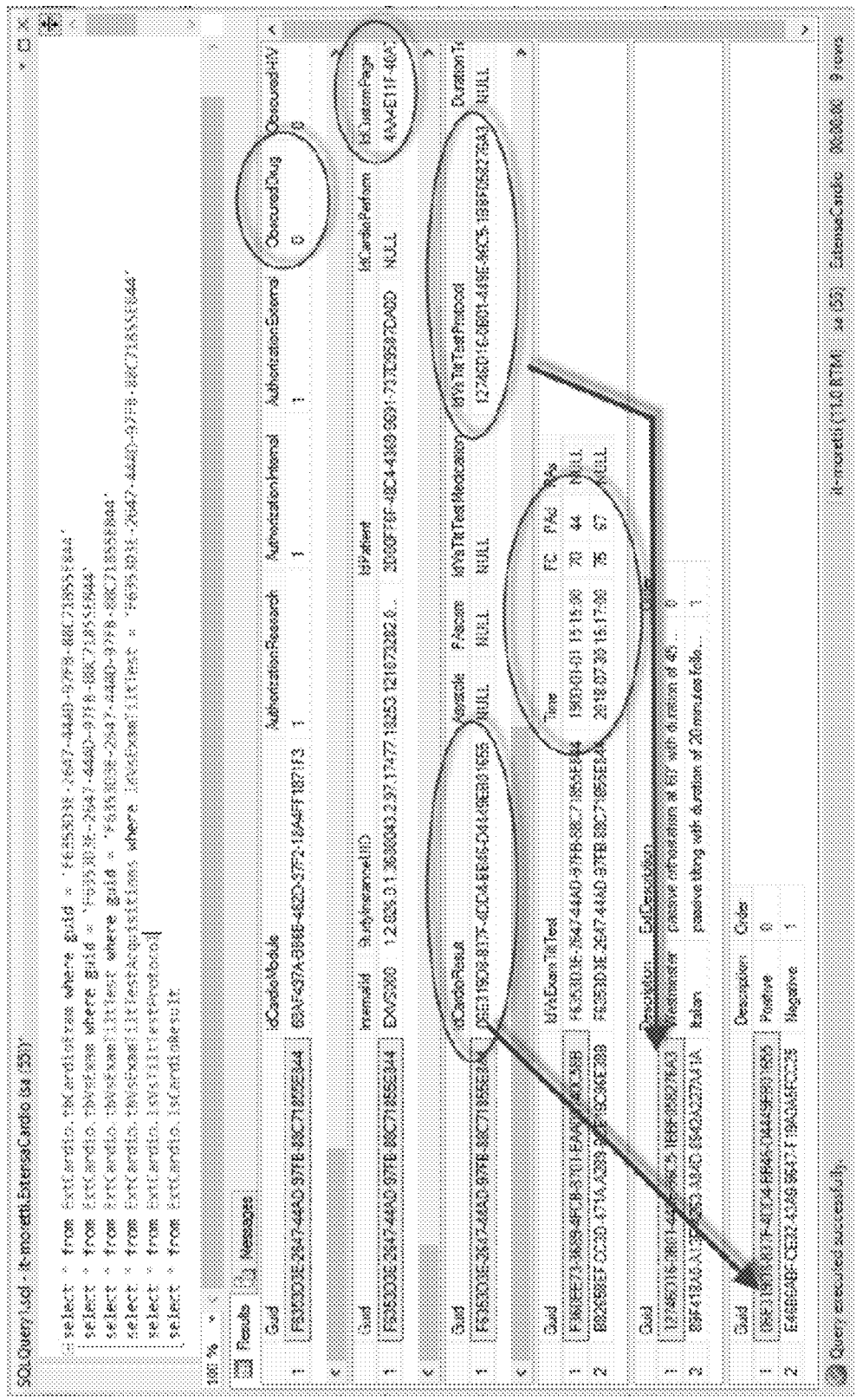
FIG. 3B illustrates a screenshot of data that may be stored in a clinical database.

FIG. 3B illustrates a screenshot of data that may be stored in a clinical database. In this example an implementation of a TiltTest data table structure is represented. A main data table VsExam" include cardio exam visits and can be considered as level 0 in this representation. The specific table "VsExamTiltTest" contains tilt test main data. It represents the level 1 and is obviously related to VsExam. TiltTest can have a cardioResult positive or negative. A detailed data table representing acquisition data VsExamTiltTestAcquisitions (level 2) is related to "VsExamTiltTest". In this example during the visit for cardio exam, the patient got a single tilt test (with a specific "Westminster" protocol and a "Positive" cardio result (IdCardioResult) with 2 acquisitions. More complex exam model (different by TiltTest) can be managed by EDSM without limit in level depth (data nesting).

Figure 3C:
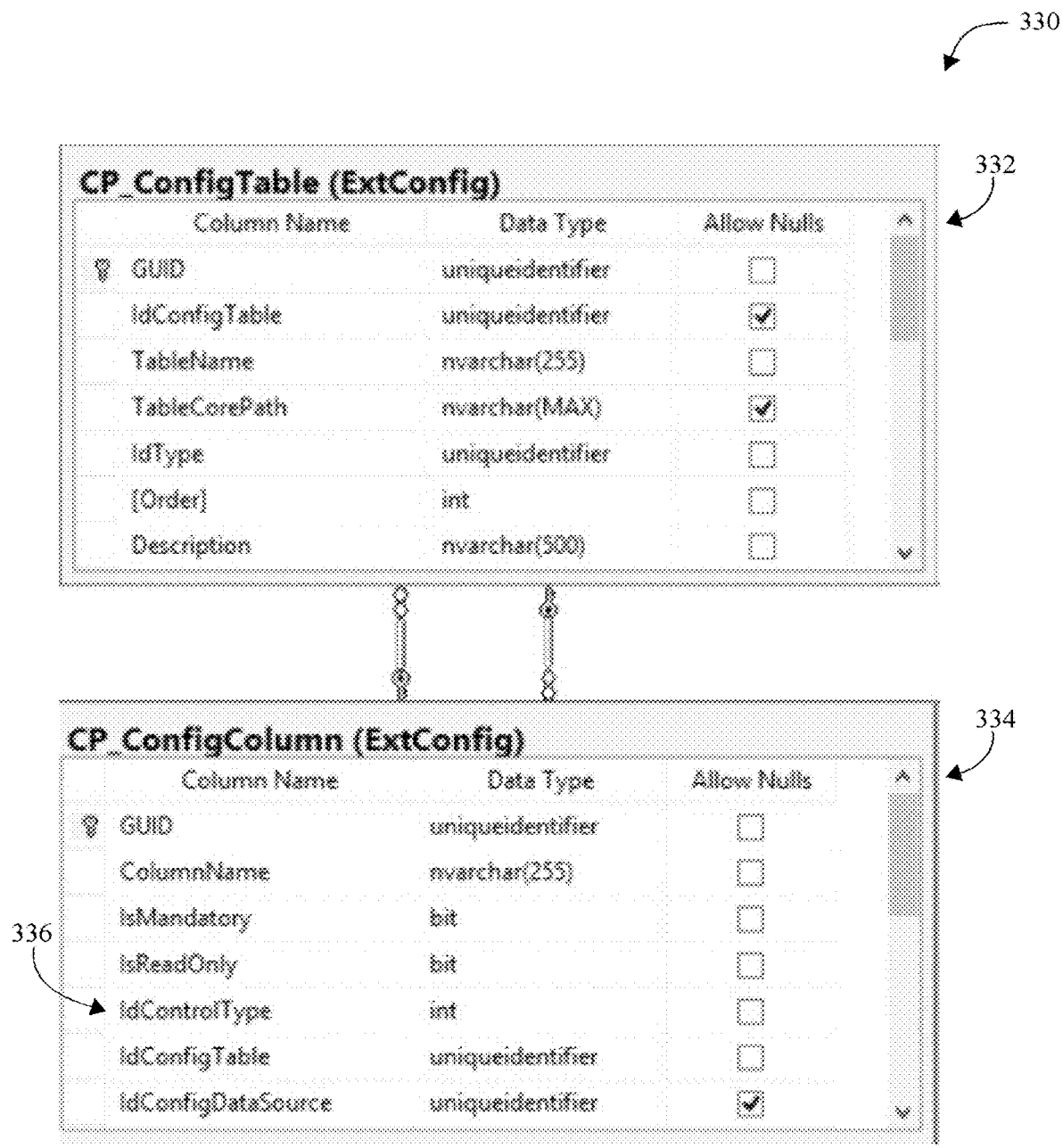
FIG. 3C illustrates examples of data structures that are created in connection with components that are defined within a custom page layout in connection with an example embodiment herein.

FIG. 3C illustrates examples of data structures (stored in custom page database) that are created in connection with components that are defined within a custom page layout in connection with an example embodiment herein. The custom page data source structure 330 may include tables. When a custom page is defined, it is necessary to indicate which tables from the clinical database will be used as source data. For example, if in the custom page "Patient data" (like "name", "surname", "birth date", etc.) will be present, it is necessary to add a row in the 332 table the reference to the Patient table of the clinical database (TableName=tbPatient, etc.). The 334 table defines which columns of the tables inserted in the 332 are of sources of interest for the specific custom pages. In the just mentioned example, we should add in 334, 3 different rows with Column name respectively equal to "name", "surname" and "birth date".

Figure 3D:
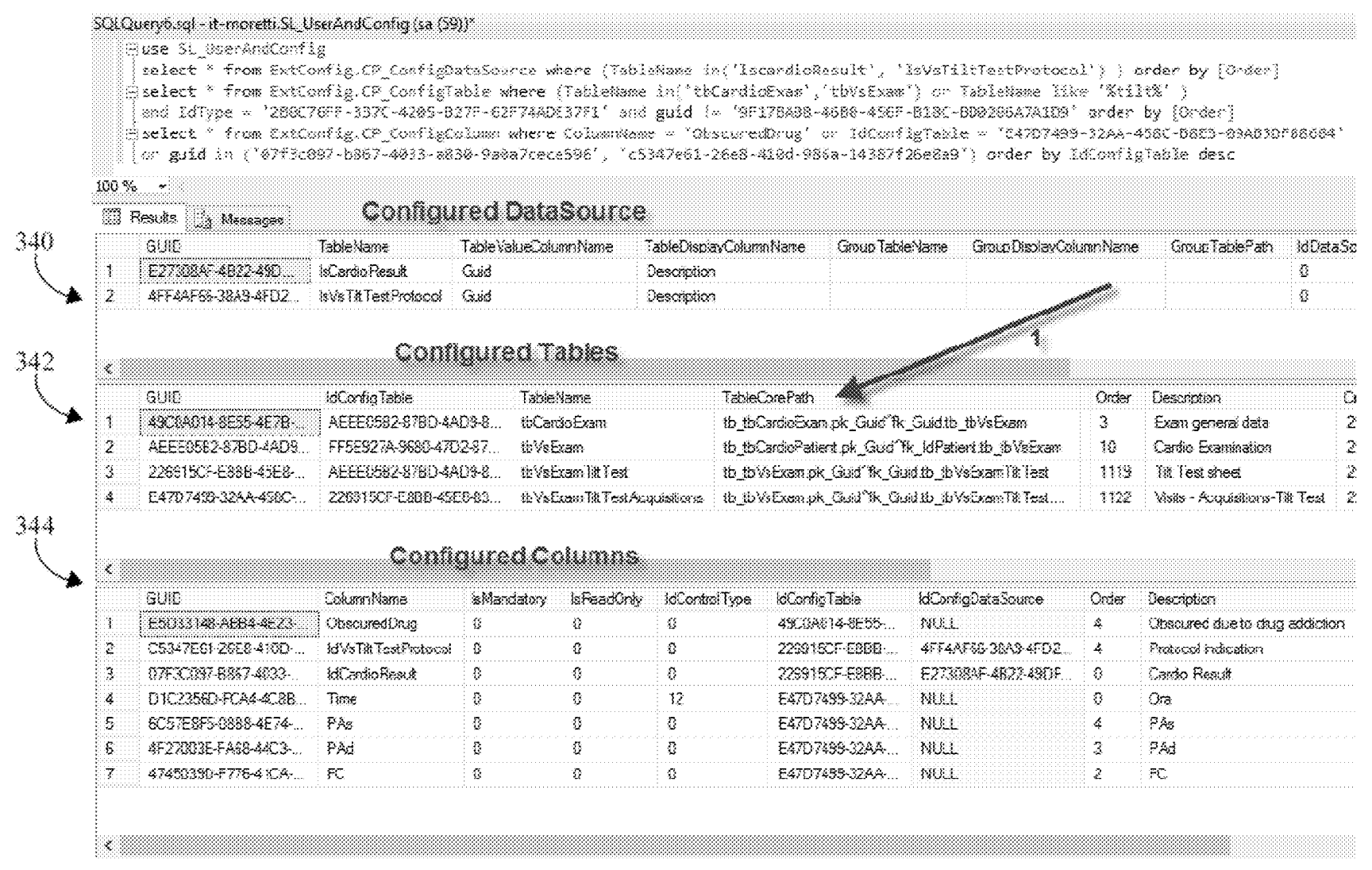

FIG. 3D illustrates a screenshot of a custom page configuration data structure. The screenshot illustrates examples of data sources 340, examples of configured tables 342 and examples of configured columns 344, all of which are configured by medical personnel (or at their instruction) during the configuration phase (stored in custom page database). The data field "table core path" is used to allow the EDSM package to understand how to obtain particular data from clinical or patient database. For example, the field "table core path" is used to automatically create a database query, such as a SQL query, that is launched into the clinical database. With reference to FIG. 3C, the "ID control type" 336 is used to define the characteristics of a column in the table, indicating whether the EDSM package may generate an editor automatically. For example, the value zero indicates that the EDSM package may automatically create an editor. Alternatively, when a different ID control type is designated, the designation may direct the EDSM package to create a specific layout control (e.g., a time control editor may be rendered at certain times).

Figure 3E:
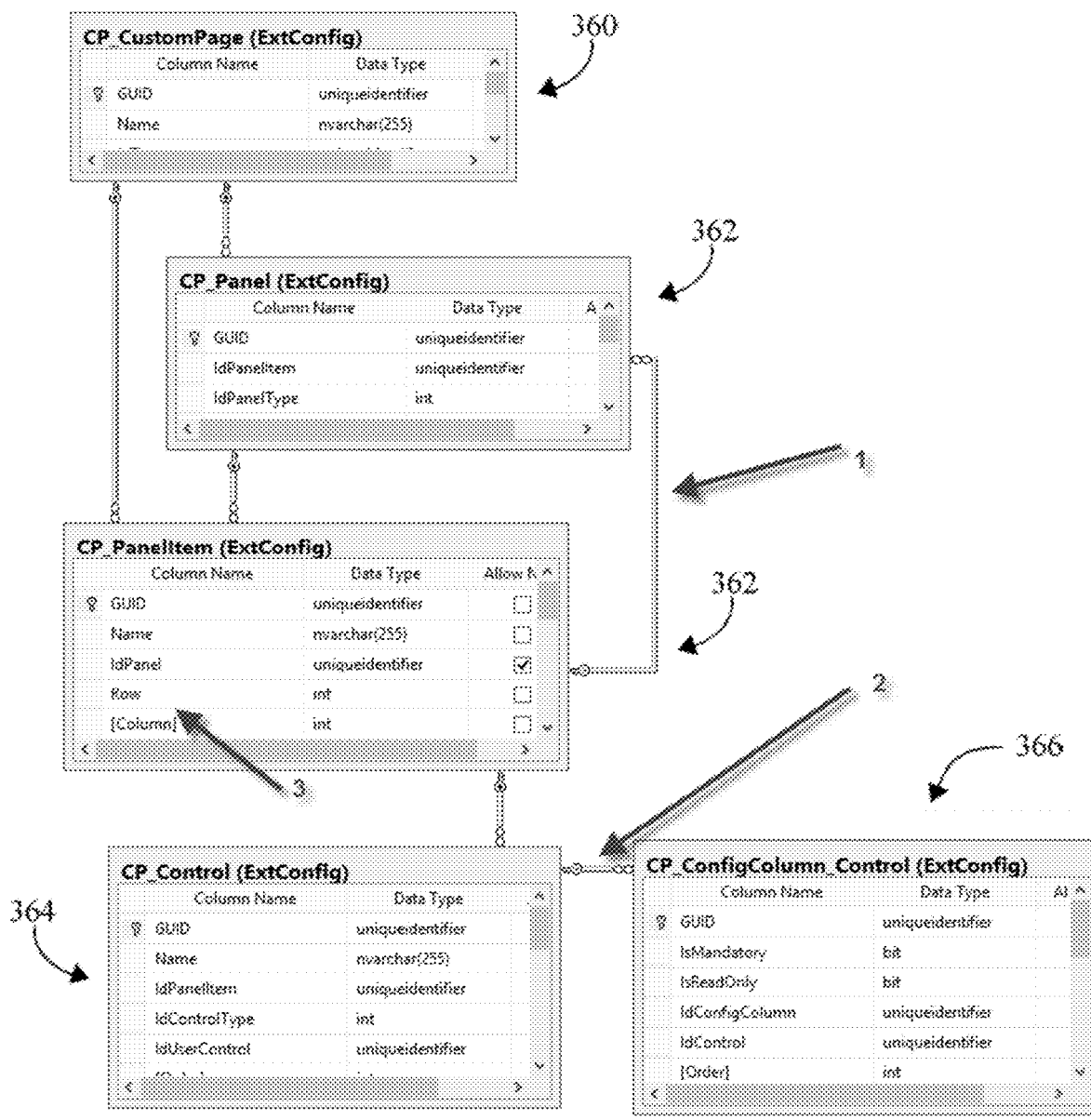
FIG. 3E illustrates examples of data structures that are created in connection with components that are defined within a custom page layout in accordance with embodiments herein.

FIG. 3E illustrates examples of data structures that are created in connection with components that are defined within a custom page layout in accordance with embodiments herein. The data structures include a main page definition 360 that defines the overall layout of the page and rendering information utilized to render the custom page into a displayable format. The data structure includes panel definitions 362 associated with each panel to be presented within the custom page. The panel definitions define a layout and format of individual panels that may be co-displayed, overlapped with one another or displayed at different times while presenting the custom page. Each panel contains one or more panel items that are arranged in a defined format (row and column). For example, each panel item may be positioned with respect to grid coordinates within a panel, where the panel item is positioned at a defined row and column index within the panel. The data structure further includes panel field definitions 364 associated with each panel item. One panel item can be associated to one or more panel fields (for example, panel item "Patient Data" is made by panel fields "Name", "Surname", "Birth Date", etc.) to be displayed within a panel and/or on the custom page. The panel field (also named "Control") definitions 364 define also the label, the layout and the format of individual panel fields For example, the panel field definition 364 may include a string variable associated with the panel field labeled "Name", Each panel item may designate another panel or one or more controls to be applied in connection with a data field.

The panel fields (controls) 364 are associated with individual and selected data to be displayed on the custom page and define how they can be edited (checkbox, free text, number, date, etc.). The data structure further includes data definitions 366 which identify the information within the clinical database and identify a relation between the clinical database information and the corresponding field (corresponding to the field definition 364). The data definition 366 defines a relationship to inform the EDSM package which data are to be connected with each rule/control within the page. The data definition 366 is related to 334 FIG. 3C (configColumn) which describe how to get data source. In Custom Page database, this is the connection between layout and data source configuration.

Figure 3F:
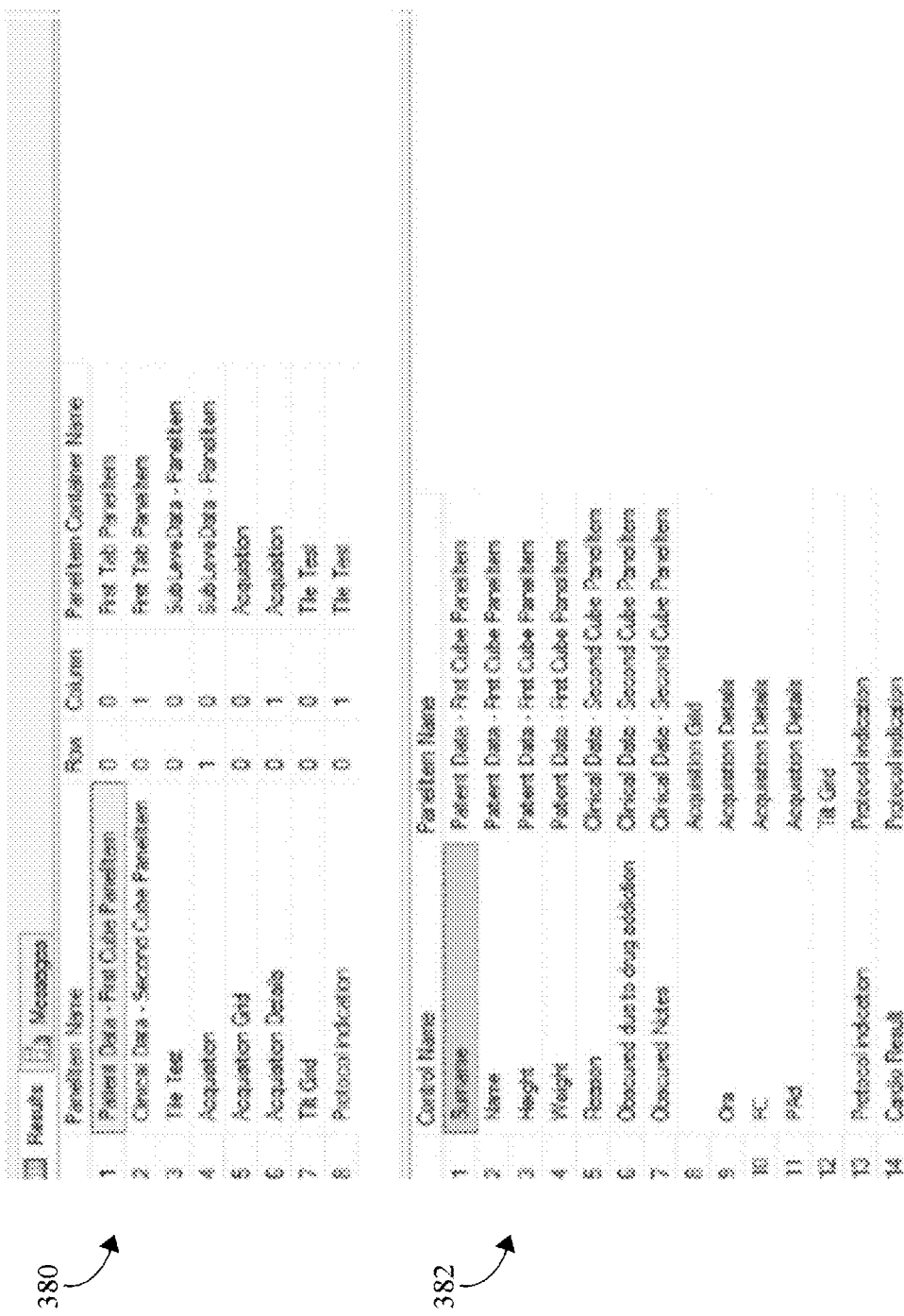
FIG. 3F illustrates a table of example panel field names and locations, as well as a table of control names and panel field associations in accordance with embodiments herein.

FIG. 3F illustrates a table 380 of example panel field names and locations, as well as a table 382 of control names and panel field associations. The table 380 includes panel field names, such as "acquisition details" and "protocol indication". The table 382 identifies in which panel items (PanelItemName) the different panel fields (control name) have to be inserted. For example, "ORA", "FC" and "PAD" will be inserted in the "Acquisition Details" panel item.

Figure 4A:
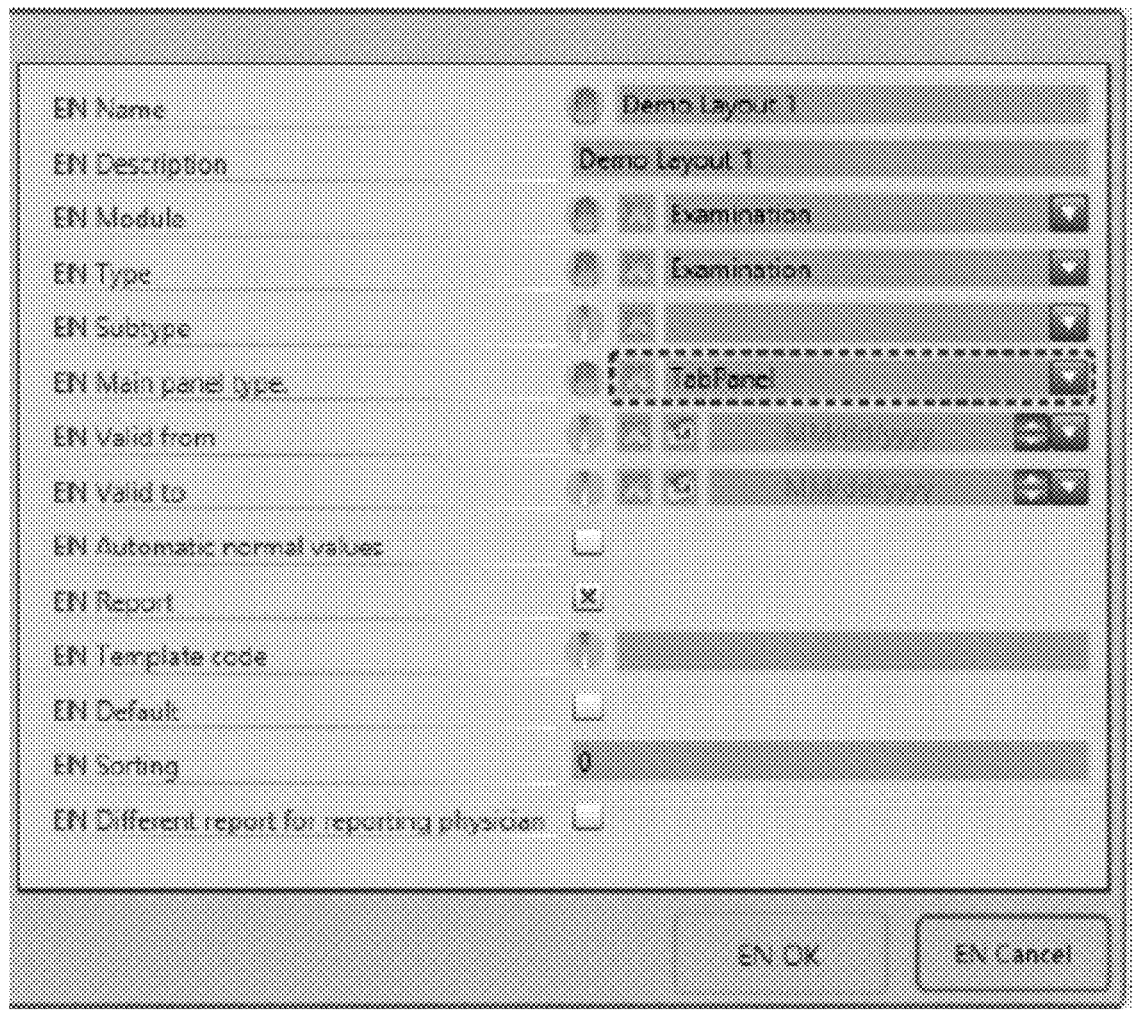
FIG. 4A illustrates an example screenshot of the window presented on the graphical user interface in connection with creating a new custom page in accordance with embodiments herein.

FIG. 4A illustrates an example screenshot of the window presented on the graphical user interface in connection with creating a new custom page. By way of example, the window allows the user to enter name, description, module, type, subtype, a main panel type, and a date range for which the panel remains valid, among other things. For example, the module and type have been designated to correspond to an examination, while the main panel type has been designated as a "tab panel". No date range has been defined yet for which the panel is valid. Each panel may contain multiple panel items, while each panel item may designate controls for patient data, other panels, etc.

Figure 4B:
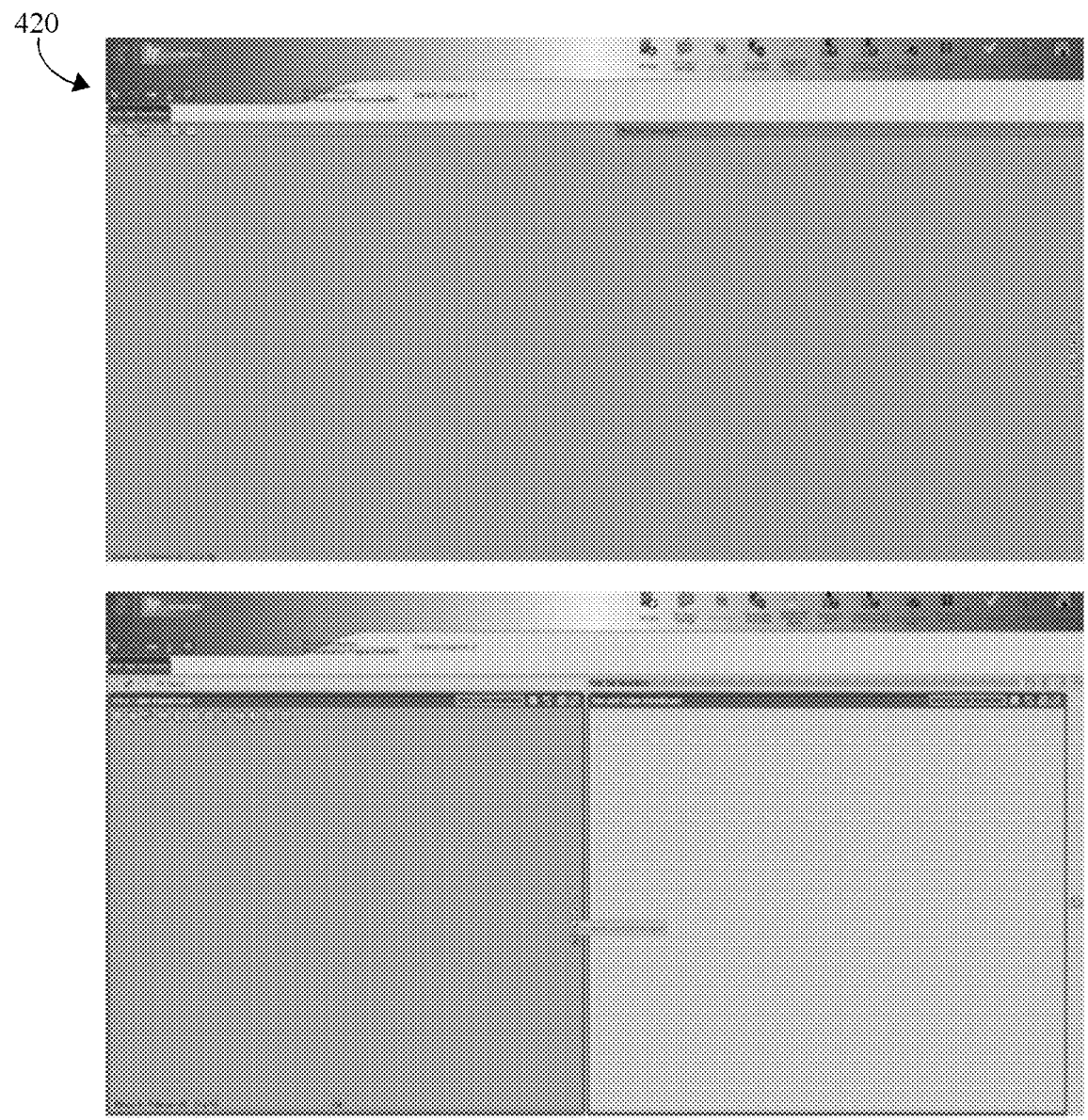
FIG. 4B illustrates a screenshot of windows presented while a user defines a panel and panel fields in accordance with embodiments herein.

FIG. 4B illustrates a screenshot of windows 410 and 411 presented while a user defines a panel and panel fields. Window 410 presents a panel that may be initially presented blank or with one or more predefined panel fields, such as based on a predefined custom page. The user is then afforded the opportunity to modify the panel and/or panel fields from the predefined custom page. As the user defines additional panel fields, the window 410 is modified, such as illustrated by the window 411 to add the additional panel fields.

Figure 4C:
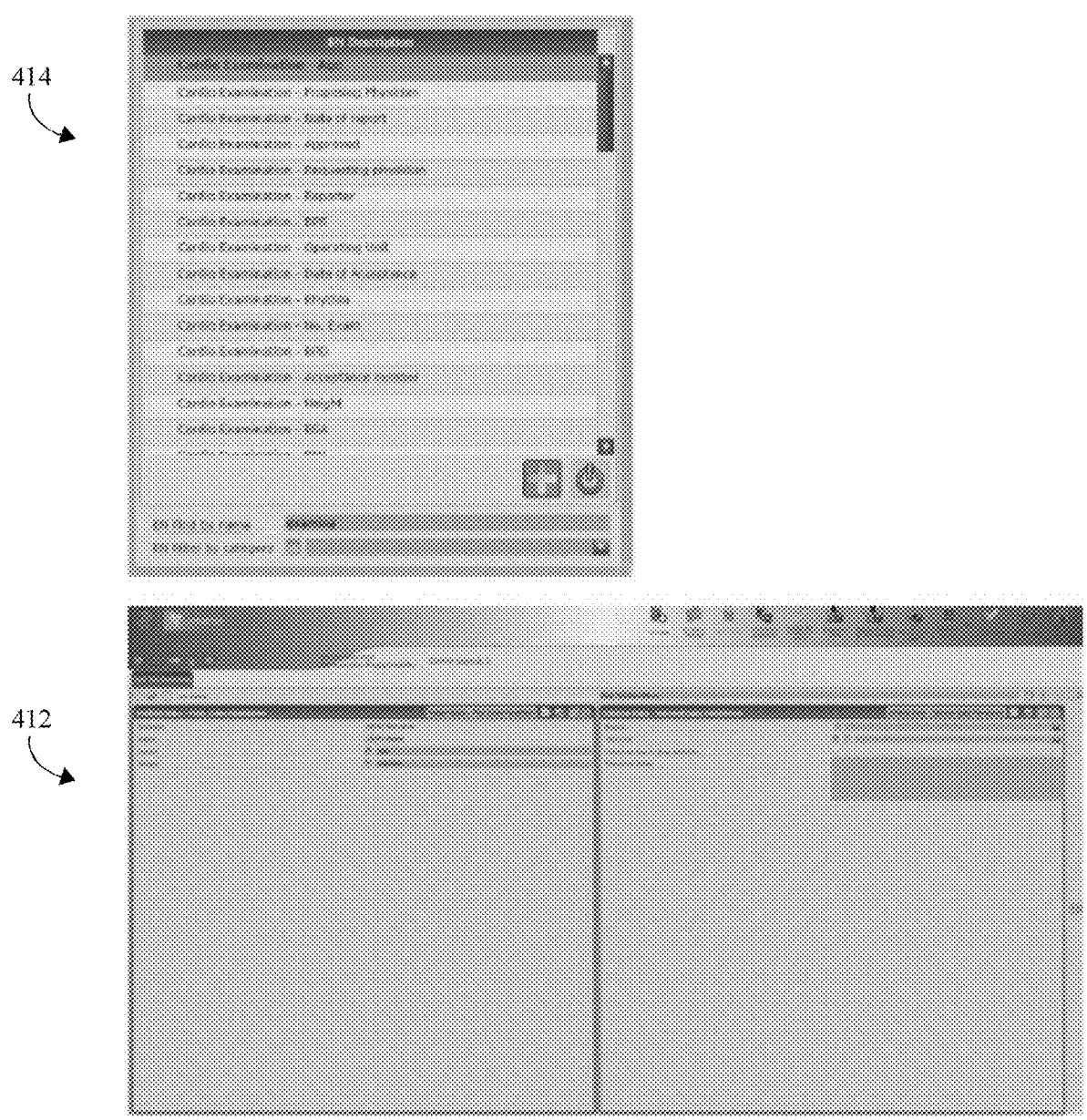
FIG. 4C illustrates the window while being modified to define panel fields to be included therein in accordance with embodiments herein.

FIG. 4C illustrates the window 412 while being modified to define panel fields to be included therein. By way of example, the panel fields may include patient name, height, weight, procedure description and the like. One or more pop-up windows, such as window 414, may be presented to allow the user to designate particular panel fields (controls) used to manipulate data within panel items. Non-limiting examples of descriptions of controls include cardiac examination—proposing physician, cardiac examination—operating unit, cardiac examination—rhythm, cardiac examination—requesting physician and the like. The term "rhythm" is the "column name" of a specific row of the table 334 (FIG. 3C). The term "cardiac examination" is the "description" at 332 corresponding to the "IDConfigTable" indicated at 334. The list of examination types for control rules, as well as other lists presented are dependent upon the type of custom page that the user has chosen. Each custom page may include a different list of descriptions of controls.

Figure 4D:
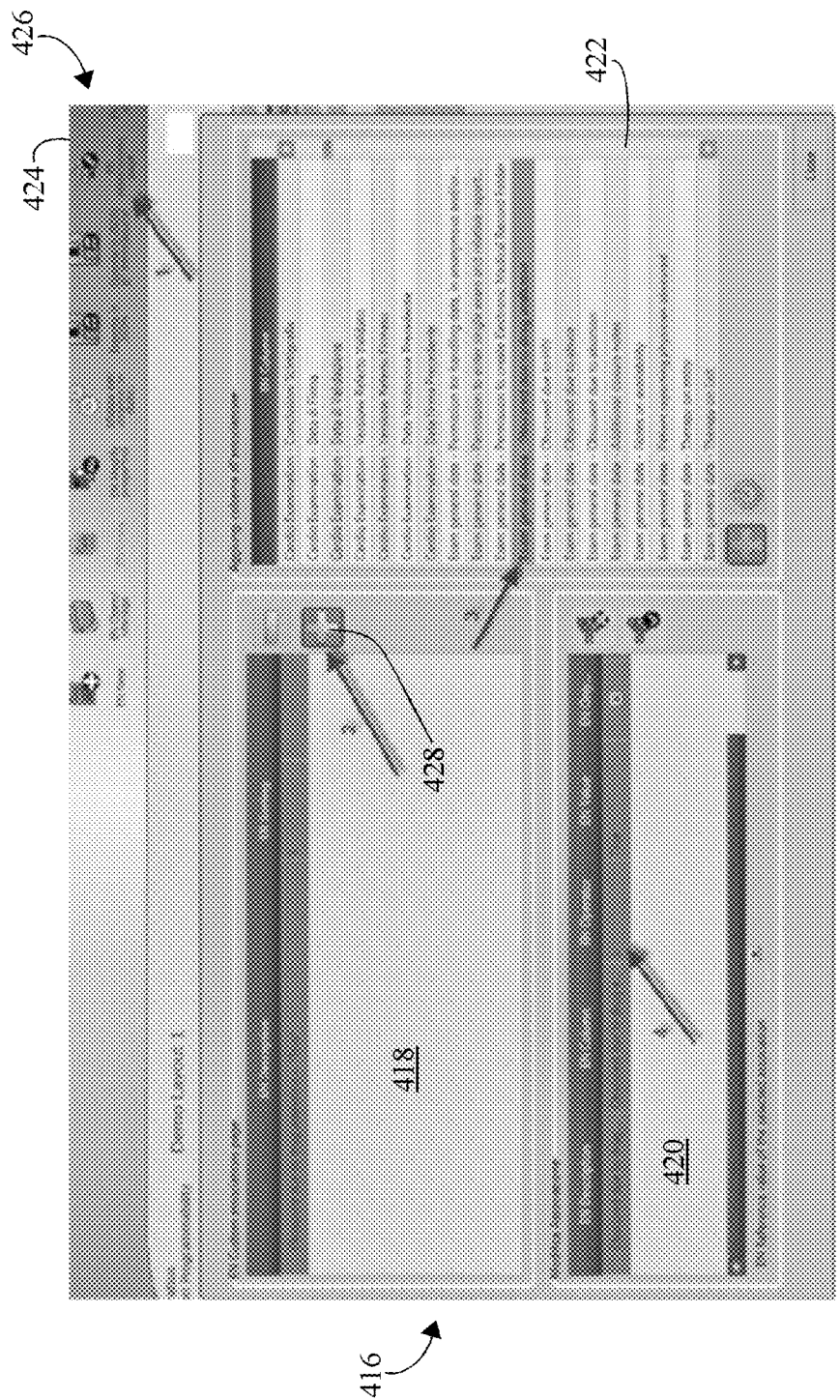
FIG. 4D illustrates a binding rule source designation window that may be presented to allow the user to enter constraint rules in connection with particular panel items and a source in the clinical database in accordance with embodiments herein.

FIG. 4D illustrates a binding rule source designation window 416 that may be presented to allow the user to enter constraint rules in connection with particular panel items (e.g., panel fields) and a source in the clinical database. The rule source designation window 416 includes a custom association zone 418, a modification association zone 420, and a list of all data fields 422 that may be associated with the rule. The rule source designation window 416 is presented in response to the selection of an association tab 424 presented along a menu bar 426. Once the association tab 424 is selected, the custom association zone 418 is presented. The user selects an "Add" tab 428, in response to which the list of available data fields 422 is presented. The user selects a constraint rule (or association) which is added to the custom association zone 418. The user is then afforded the option to modify the association within zone 420, such as by changing an operator, value or other characteristics associated with the rule.

Figure 4E:
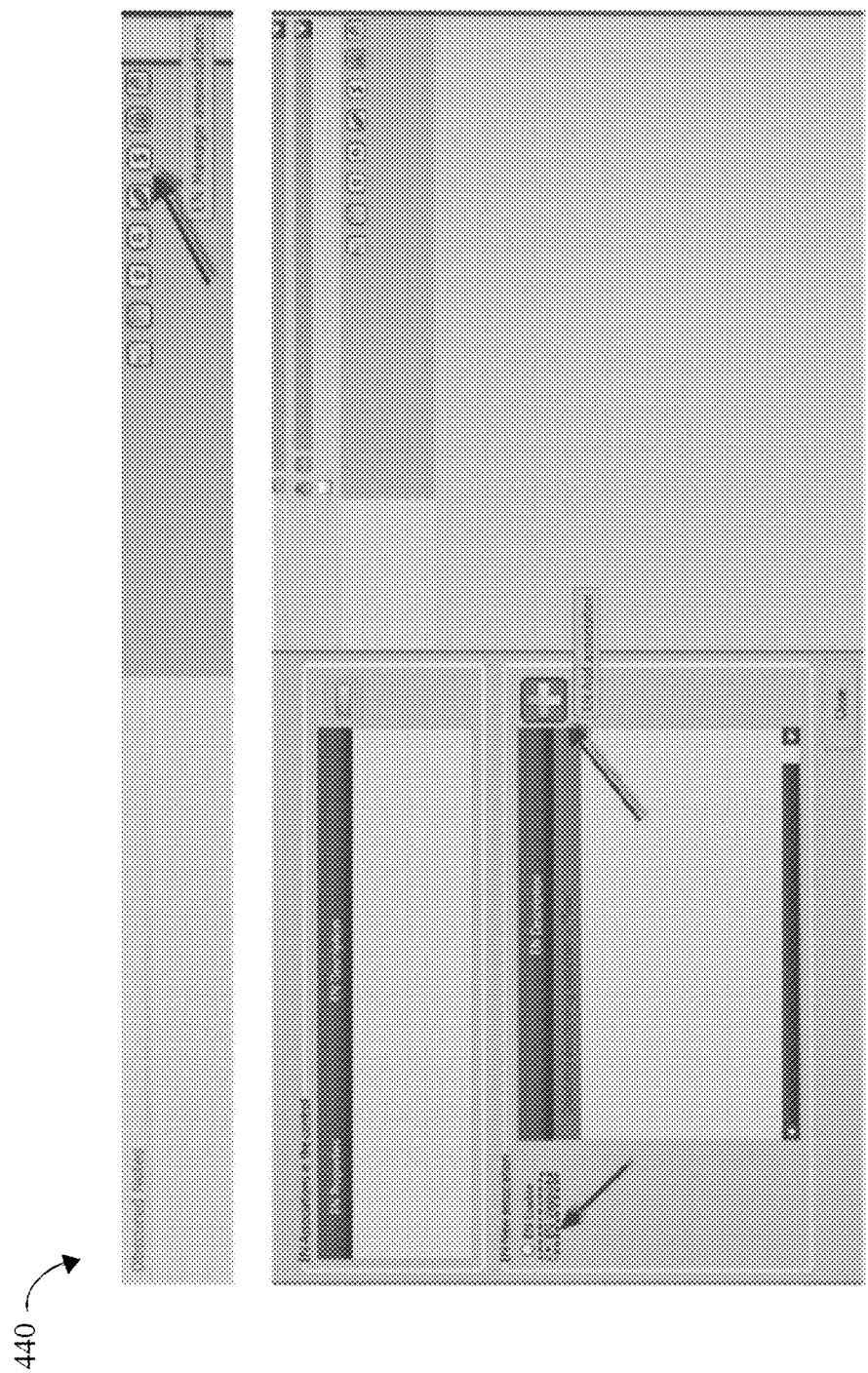
FIG. 4E illustrates a rule update window that may be utilized in connection with associating a panel field to another control, panel field, etc. in accordance with embodiments herein

FIG. 4E illustrates a rule update window 440 that may be utilized in connection with associating a panel field to another control, panel field, etc. In the example of FIG. 4E, the additional control relates to switching a data entry field between a visible state and a hidden state.

Figure 5A:
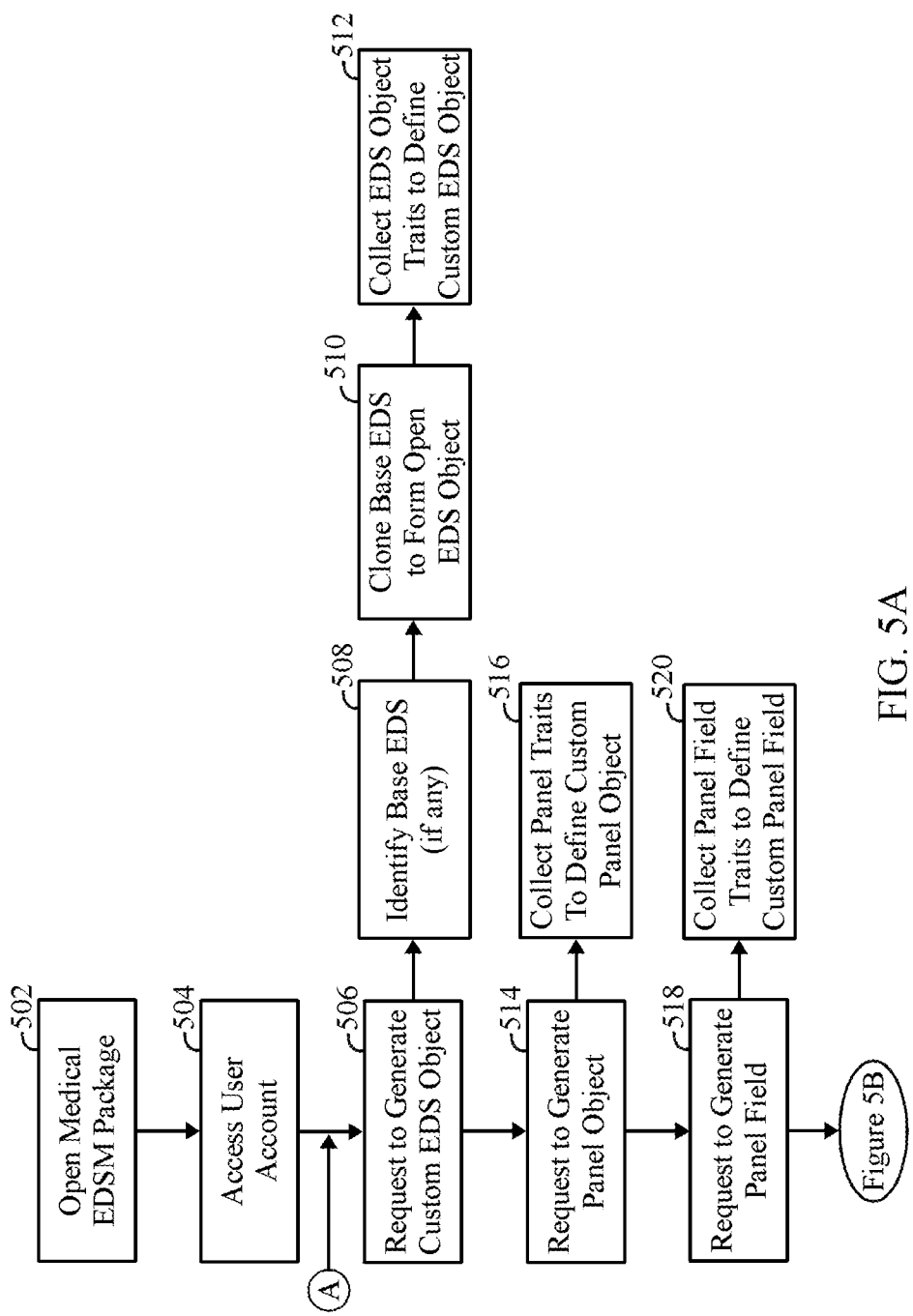
FIG. 5A illustrates a process for creating customized medical electronic data sheets in accordance with embodiments herein.
Figure 5B:
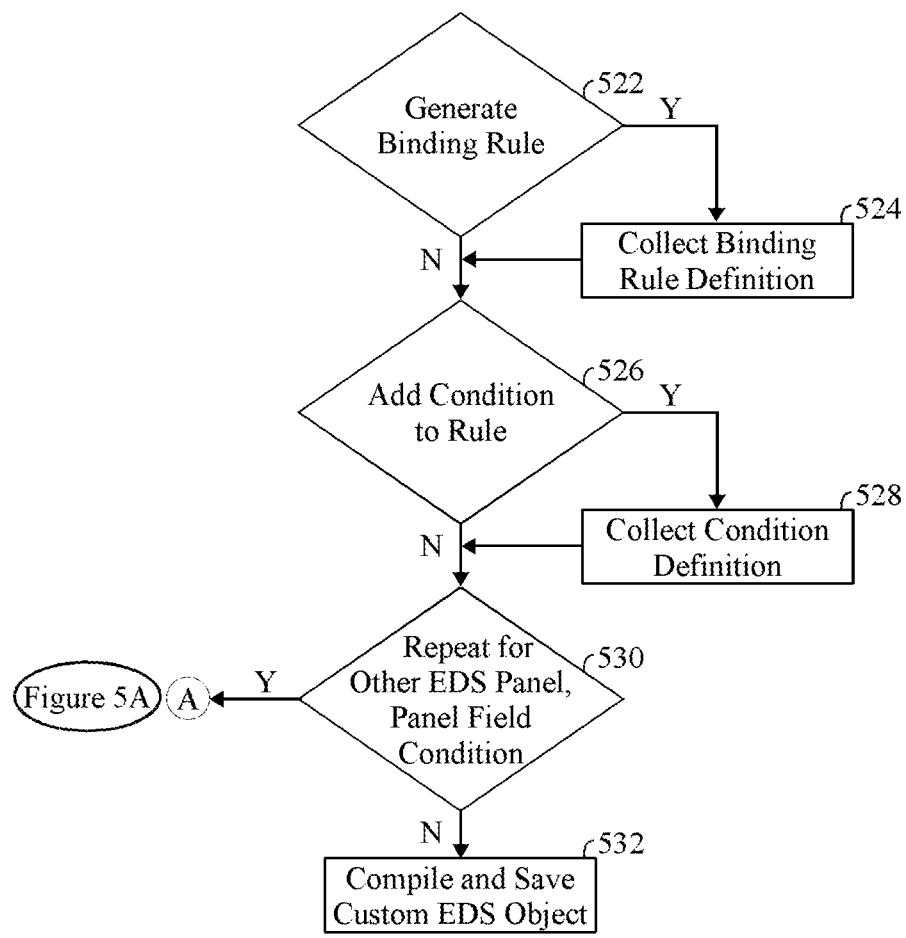
FIG. 5B illustrates a process for creating customized medical electronic data sheets in accordance with embodiments herein.

FIGS. 5A and 5B illustrate a process for creating customized medical electronic data sheets in accordance with embodiments herein. At 502, one or more processors of the implementation computer system open the medical EDSM package. At 504, the one or more processors access a user account, such as based on a user to login. It is recognized that the operations of FIGS. 5A and 5B are not necessarily performed in a serial manner, but instead may be performed in parallel and/or other orders based on request by the user. It is also recognized that certain operations may be skipped or omitted based upon user inputs.

At 506, the one or more processors receive a request to generate a custom EDS object, such as an EDS page. At 508, the one or more processors attempt to identify a base EDS object, if one is available, to utilize as a starting point for the custom EDS object. For example, the processors may attempt to identify a base EDS object based on a type of examination, medical procedure, anatomical structure of interest, imaging modality and the like. As a further example, the request may concern creation of an EDS object related to a particular type of anatomical pathology, such as blockage of an artery on the heart. At 508, the one or more processors determine whether a base EDS object exists that is related to arterial blockage. When a base EDS object is identified, the base EDS object is presented to the user through the graphical user interface. The user is afforded the option to use the base EDS object in an unmodified form or to create a custom EDS object. The base EDS object is locked to prevent the user from modifying the base EDS object. When the user desires to customize the base EDS object, flow moves to 510. At 510, the one or more processors clone the base EDS object to form an editable or open EDS object that the user may modify.

At 512, the one or more processors monitor interactive operations by the user while editing the EDS object. Each time the user makes a modification to the EDS object, the modifications are collected as EDS traits that define the custom EDS object. Non-limiting examples of EDS object traits include tab panel (each label in tab panel layout correspond to a panel item which contains one panel object or data fields) or cube/grid panel object (traits described by rows and columns. The one or more processors may perform the operations at 512 in series and/or parallel with the remaining operations of FIGS. 5A and 5B.

At 514, the one or more processors determine whether a request has been received to generate a new panel within an EDS page. When a request is received to add a new panel, flow moves to 516. At 516, the one or more processors collect panel traits to add to the new panel object that defines the new panel to be displayed on the GUI.

At 518, the one or more processors determine whether a request has been received to generate a new panel field within a new panel. If so, flow branches to 520. At 520, the one or more processors collect panel field traits that define the new panel field. Flow continues to FIG. 5B.

With reference to FIG. 5B, at 522, the one or more processors determine whether a request has been received to generate a binding rule. If not, flow continues to 526. If so, flow moves to 524. At 524, the one or more processors collect binding rule definition information in connection with one or more rules. The binding rule definition information defines a binding relation between one or more clinical data values and one or more panel fields. The binding rules designate operations to be automatically performed based on the clinical data values entered into the associated one or more panel fields. Next, flow continues to 526.

At 526, the one or more processors determine whether an additional condition is to be added to a binding rule. If not, flow continues to 530. If so, flow moves to 528. At 528, the one or more processors collect condition definition information to be added to one or more associated rules. By way of example, the condition may be to hide or expose a panel field based upon data values that are entered in another panel field. Next, flow continues to 530.

At 530, the one or more processors determine whether a request has been received to repeat the foregoing operations in connection with another page, additional panels associated with the current page, additional panel fields associated with the current panel, additional conditions and the like. If so, flow returns to 506 in FIG. 5A. Otherwise, flow continues to 532. At 532, the one or more processors perform any appropriate final compiling operations in connection with defining the custom EDS object and save (local cache) the custom EDS object. For example, the newly created custom EDS object may be saved in connection with the present user's account and/or more generally made available to all medical personnel within the present medical network.

Figure 6:
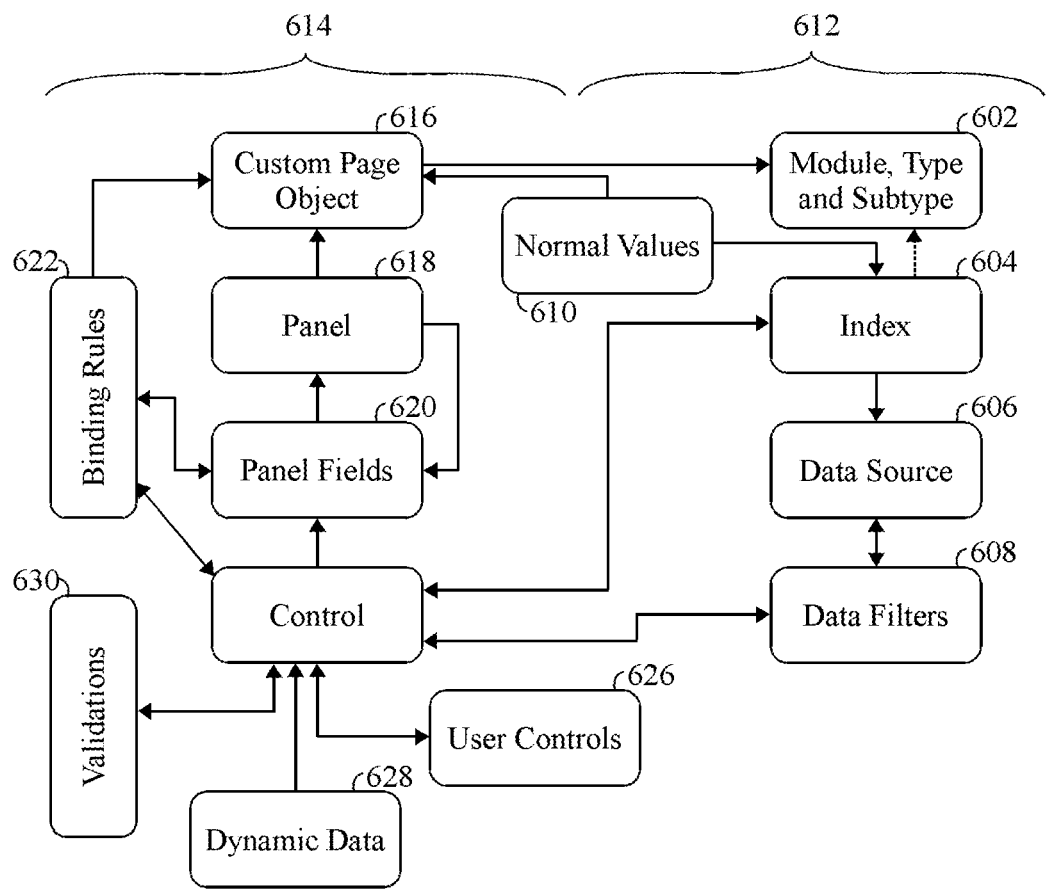
FIG. 6 illustrates a block diagram of various functional modules, data structure components and data sources within an EDSM system in connection with embodiments herein.

FIG. 6 illustrates a block diagram of various functional modules, data structure components and data sources within an EDSM system in connection with embodiments herein. FIG. 6 is generally divided into database 612 and nested EDS database structures 614. There are 4 macro areas of information stored inside the database 612 and nested EDS database structures 614, namely data, metadata, constraints and additional features. The database 612 includes all necessary information to identify a specific datum, such as an index (e.g., the table and the column) where the datum is stored, the module associated with the datum, the type associated with the datum, the subtype and the data sources or filters linked to the datum. When the data sources are arranged in tables, the tables are also linked with one another and an entire relational schema is stored inside the database (this includes the paths from the root to each table in order to allow any chain of nested data). Each type has a root table so there is a specific and unique dataset assigned to each type and nested EDS database structure.

The database 612 includes the data sources and data structures describing the organizational structure of the data sources 606. For example, the elements within the database 612 may be stored in one or more databases. The data sources 606 may include any and all types of patient data, such as patient information, examination results, diagnostic images, therapy related information). The data sources may be organized in a known structure. The content of the data sources 606 is organized and located based on index information 604. For example, the index information 604 may identify individual tables, rows within tables, columns within tables and the like, where specific clinical data values are stored. The data sources may be further divided based on module, type and subtype 602. For example, a module may indicate radiology, cardiology or otherwise, a type may indicate a particular reporting module (inside the cardiology module, for example: hemodynamics, echocardiography, arrhythmology, etc.), while a subtype may indicate a subset of procedures to be reported (inside the echocardiography, for example, there are: transthoracic echocardiography, transesophageal echocardiography, stress test, etc.). It is recognized that the data sources may be divided in other manners. Normal or reference clinical data values 610 may be maintained. For example, a normal clinical data value 610 may represent a baseline value measured for a particular patient or for a group of patients.

Data filters 608 may be provided to facilitate filtering of the data sources 606. For example the TiltTest can have only a "positive" or "negative" result (FIG. 3B). The source of possible values of the panel field "Result" is the clinical data table "IsCardioResult" (Data Source) but it may contain more values than "positive" and "negative", for example "negative with warning", "exam to be repeated", and so on. So, it is possible to add a rule (filter) that shows just in this specific case only 2 possible values from all the values available in the source table. In general, each DataSource can be filtered to show only what is needed, and the filters assume the role of constraints, likewise binding rules, validation and calculation formulas.

The nested EDS database structures 614 are illustrated in terms of data structure components and functional modules that are defined by a user when constructing custom EDS objects and reporting pages. Each custom EDS object is associated with a reporting module. Non-limiting examples of reporting modules include check-ups, endoscopy, cardio surgery, and the like. A non-limiting example of a reporting module type is pediatric cardiology checkup. Among other things, custom EDS pages (objects) 616 are defined that include one or more panel objects 618, where the panel objects 618 include one or more panel fields 620. Binding rules 622 are generated in connection with the panel fields. User controls 626 and dynamic data 628 may also be defined within the custom EDS object. A validation functional block 630 is provided in connection with validating data values and/or other content of panel items.

Examples of control data formats are date, numbers (integers or decimals), strings, formatted text, formatted text with predefined sentences, flags, currencies, multiple selection structures (combinations), data grid structures. Metadata information describes how a custom page is rendered from an EDS object. Each new custom page has a root panel. A panel is a container of panel fields, where each panel field may contain a link to a data value, a link to another panel and/or one or more controls. Each panel, panel field and control contains any useful information needed to be correctly rendered such as positioning, type or label. For example, each control is linked to one or more columns and the association of the control with the one or more columns determines at least a portion of the behavior of the controls. For example, if a control is linked to three columns then the control will be rendered as a three-column grid.

Additionally or alternatively, a control may be associated with dynamic data created by the user and/or can be a predetermined non-dynamic complex control (e.g., user control written by software developers). The use of predetermined non-dynamic complex controls may be useful when an EDS page has to contain very complex parts that include some automation whose behavior is not included in the EDSM package.

Embodiments herein provide a notification constraint module that affords a substantial improvement over conventional electronic data sheet systems. The constraint is essentially a rule on a specific dataset. The basic idea is that changing a data value can cause some actions. These actions can be very different from one another and can include data validation, filtering, automatic calculations or user interface actions. For example, as a consequence of a specific data change, a panel could be hidden, or the associated control could be put in error. In addition, it is also possible to specify a condition (that is a type of constraint) in order to obtain complex behaviors such as cross data validation (for example, a specific data becomes mandatory only when another data has a certain value).

Additionally or alternatively, a string of utilities may be provided which do not have a direct impact on the notification constraint module operability, but improve the usability of the notification constraint module. An example could be "normal values". Each data entry field could indeed be associated to a normal (or default) value. Then, with a click on a button inside the page, it will be possible to automatically pre-set the data and reduce the amount of manual data entry.

Figure 7:
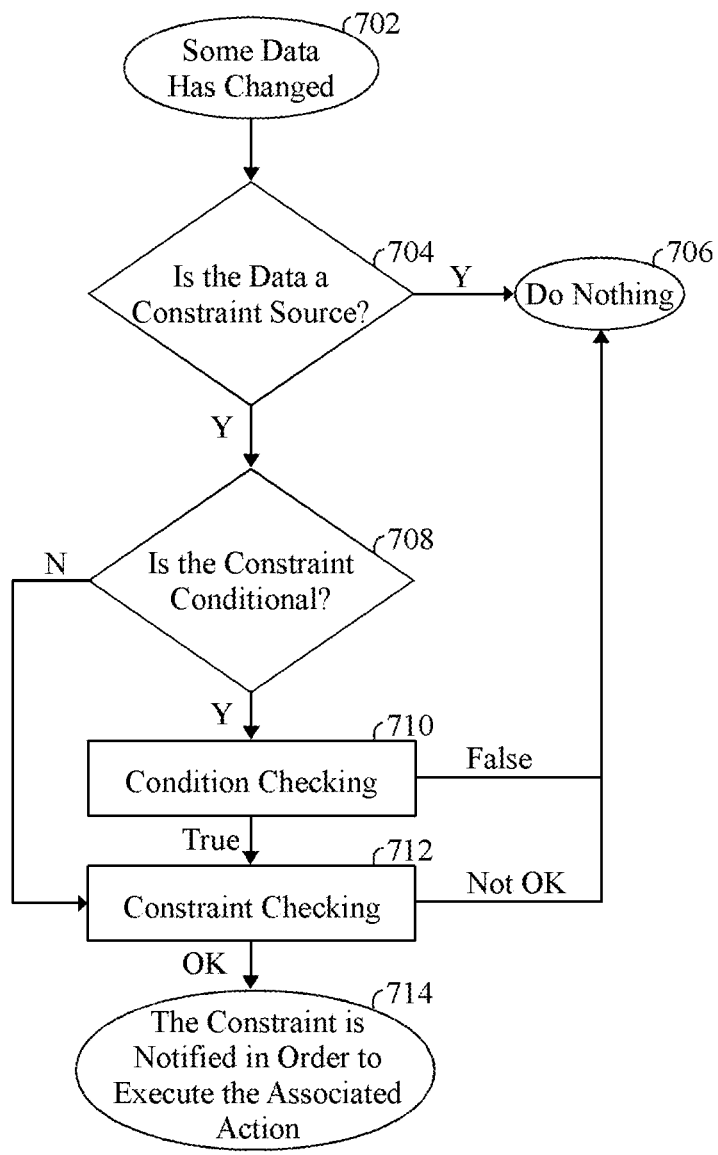
FIG. 7 illustrates a process utilized while navigating through a custom EDS object as patient data is entered/modified in accordance with embodiments herein.

FIG. 7 illustrates a process utilized while navigating through a custom EDS object as patient data is entered/modified. At 702, the one or more processors determine whether a data value within the custom EDS object has been changed. For example, a blank field may be populated with new clinical data and/or pre-existing clinical data may be changed for an individual patient. At 704, the one or more processors determine whether the changed data corresponds to a constrained data source.

If not, flow moves to 706 and no further action is taken. Alternatively, when the changed data corresponds to a constrained data source, flow moves to 708. At 708, the one or more processors determine whether the constraint related to the data source is conditional.

When the constraint is not conditional, flow skips to 712. Otherwise, when the constraint is conditional, flow continues to 710. At 710, the one or more processors check the condition to determine whether the condition is false or true. When the condition related to the constraint is false, flow moves to 706 and no further action is taken. Alternatively, when the condition related to the constraint is true, flow continues to 712.

At 712, the one or more processors check the constraint to determine whether the constraint is satisfied. When the constraint is not satisfied, flow moves to 706 and no further action is taken. Alternatively, when the constraint is satisfied, flow moves to 714. At 714, the one or more processors execute an action associated with the constraint.

For example, the process of FIG. 7 may be implemented in connection with a constraint regarding whether the patient is a smoker. At 702, the medical personnel enter a designation that a patient is a smoker. At 704, the processors determine that the "smoker" designation data is a constraint source (e.g., source of a rule), and therefore flow moves to 708. At 708, the processors determine that a condition exists that subordinates the constraint (e.g., if the patient is a smoker), and therefore flow moves to 710. At 710, the processors determine that the medical personnel have specified that the patient is a smoker, so the condition is TRUE, and flow moves to 712. At 712, the processors check information regarding how many years the patient has smoked, and the result is passed to 714. At 714, the processors set a status of an associated record (e.g., in error or not) depending the results of the determine that the condition and constraint (e.g., is the patient a smoker) are true and thus flow moves to 714.

CONCLUSIONS

It should be clearly understood that the various arrangements and processes broadly described and illustrated with respect to the FIGS., and/or one or more individual components or elements of such arrangements and/or one or more process operations associated of such processes, can be employed independently from or together with one or more other components, elements and/or process operations described and illustrated herein. Accordingly, while various arrangements and processes are broadly contemplated, described and illustrated herein, it should be understood that they are provided merely in illustrative and non-restrictive fashion, and furthermore can be regarded as but mere examples of possible working environments in which one or more arrangements or processes may function or operate.

Aspects are described herein with reference to the FIGS., which illustrate example methods, devices and program products according to various example embodiments. These program instructions may be provided to a processor of a general purpose computer, special purpose computer, or other programmable data processing device or information handling device to produce a machine, such that the instructions, which execute via a processor of the device implement the functions/acts specified. The program instructions may also be stored in a device readable medium that can direct a device to function in a particular manner, such that the instructions stored in the device readable medium produce an article of manufacture including instructions which implement the function/act specified. The program instructions may also be loaded onto a device to cause a series of operational steps to be performed on the device to produce a device implemented process such that the instructions which execute on the device provide processes for implementing the functions/acts specified.

One or more of the operations described above in connection with the methods may be performed using one or more processors. The different devices in the systems described herein may represent one or more processors, and two or more of these devices may include at least one of the same processors. In one embodiment, the operations described herein may represent actions performed when one or more processors (e.g., of the devices described herein) execute program instructions stored in memory (for example, software stored on a tangible and non-transitory computer readable storage medium, such as a computer hard drive, ROM, RAM, or the like).

The processor(s) may execute a set of instructions that are stored in one or more storage elements, in order to process data. The storage elements may also store data or other information as desired or needed. The storage element may be in the form of an information source or a physical memory element within the controllers and the controller device. The set of instructions may include various commands that instruct the controllers and the controller device to perform specific operations such as the methods and processes of the various embodiments of the subject matter described herein. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to user commands, or in response to results of previous processing, or in response to a request made by another processing machine.

The controller may include any processor-based or microprocessor-based system including systems using microcontrollers, reduced instruction set computers (RISC), application specific integrated circuitry (ASICs), field-programmable gate arrays (FPGAs), logic circuitry, and any other circuit or processor capable of executing the functions described herein. When processor-based, the controller executes program instructions stored in memory to perform the corresponding operations. Additionally or alternatively, the controllers and the controller device may represent circuitry that may be implemented as hardware. The above examples are exemplary only, and are thus not intended to limit in any way the definition and/or meaning of the term "controller."

Optionally, aspects of the processes described herein may be performed over one or more networks one a network server. The network may support communications using any of a variety of commercially-available protocols, such as Transmission Control Protocol/Internet Protocol ("TCP/IP"), User Datagram Protocol ("UDP"), protocols operating in various layers of the Open System Interconnection ("OSI") model, File Transfer Protocol ("FTP"), Universal Plug and Play ("UpnP"), Network File System ("NFS"), Common Internet File System ("CIFS") and AppleTalk. The network can be, for example, a local area network, a wide-area network, a virtual private network, the Internet, an intranet, an extranet, a public switched telephone network, an infrared network, a wireless network, a satellite network and any combination thereof.

In embodiments utilizing a web server, the web server can run any of a variety of server or mid-tier applications, including Hypertext Transfer Protocol ("HTTP") servers, FTP servers, Common Gateway Interface ("CGI") servers, data servers, Java servers, Apache servers and business application servers. The server(s) also may be capable of executing programs or scripts in response to requests from user devices, such as by executing one or more web applications that may be implemented as one or more scripts or programs written in any programming language, such as Java®, C, C # or C++, or any scripting language, such as Ruby, PHP, Perl, Python or TCL, as well as combinations thereof. The server(s) may also include database servers, including without limitation those commercially available from Oracle®, Microsoft®, Sybase® and IBM® as well as open-source servers such as MySQL, Postgres, SQLite, MongoDB, and any other server capable of storing, retrieving and accessing structured or unstructured data. Database servers may include table-based servers, document-based servers, unstructured servers, relational servers, non-relational servers or combinations of these and/or other database servers.

The embodiments described herein may include a variety of data stores and other memory and storage media as discussed above. These can reside in a variety of locations, such as on a storage medium local to (and/or resident in) one or more of the computers or remote from any or all of the computers across the network. In a particular set of embodiments, the information may reside in a storage-area network ("SAN") familiar to those skilled in the art. Similarly, any necessary files for performing the functions attributed to the computers, servers or other network devices may be stored locally and/or remotely, as appropriate. Where a system includes computerized devices, each such device can include hardware elements that may be electrically coupled via a bus, the elements including, for example, at least one central processing unit ("CPU" or "processor"), at least one input device (e.g., a mouse, keyboard, controller, touch screen or keypad) and at least one output device (e.g., a display device, printer or speaker). Such a system may also include one or more storage devices, such as disk drives, optical storage devices and solid-state storage devices such as random access memory ("RAM") or read-only memory ("ROM"), as well as removable media devices, memory cards, flash cards, etc.

Such devices also can include a computer-readable storage media reader, a communications device (e.g., a modem, a network card (wireless or wired), an infrared communication device, etc.) and working memory as described above. The computer-readable storage media reader can be connected with, or configured to receive, a computer-readable storage medium, representing remote, local, fixed and/ or removable storage devices as well as storage media for temporarily and/or more permanently containing, storing, transmitting and retrieving computer-readable information. The system and various devices also typically will include a number of software applications, modules, services or other elements located within at least one working memory device, including an operating system and application programs, such as a client application or web browser. It should be appreciated that alternate embodiments may have numerous variations from that described above. For example, customized hardware might also be used and/or particular elements might be implemented in hardware, software (including portable software, such as applets) or both. Further, connection to other computing devices such as network input/output devices may be employed.

Various embodiments may further include receiving, sending, or storing instructions and/or data implemented in accordance with the foregoing description upon a computer-readable medium. Storage media and computer readable media for containing code, or portions of code, can include any appropriate media known or used in the art, including storage media and communication media, such as, but not limited to, volatile and non-volatile, removable and non-removable media implemented in any method or technology for storage and/or transmission of information such as computer readable instructions, data structures, program modules or other data, including RAM, ROM, Electrically Erasable Programmable Read-Only Memory ("EEPROM"), flash memory or other memory technology, Compact Disc Read-Only Memory ("CD-ROM"), digital versatile disk (DVD) or other optical storage, magnetic cassettes, magnetic tape, magnetic disk storage or other magnetic storage devices or any other medium which can be used to store the desired information and which can be accessed by the system device. Based on the disclosure and teachings provided herein, a person of ordinary skill in the art will appreciate other ways and/or methods to implement the various embodiments.

The specification and drawings are, accordingly, to be regarded in an illustrative rather than a restrictive sense. It will, however, be evident that various modifications and changes may be made thereunto without departing from the broader spirit and scope of the invention as set forth in the claims.

Other variations are within the spirit of the present disclosure. Thus, while the disclosed techniques are susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions and equivalents falling within the spirit and scope of the invention, as defined in the appended claims.

The use of the terms "a" and "an" and "the" and similar referents in the context of describing the disclosed embodiments (especially in the context of the following claims) are to be construed to cover both the singular and the plural, unless otherwise indicated herein or clearly contradicted by context. The terms "comprising," "having," "including" and "containing" are to be construed as open-ended terms (i.e., meaning "including, but not limited to,") unless otherwise noted. The term "connected," when unmodified and referring to physical connections, is to be construed as partly or wholly contained within, attached to or joined together, even if there is something intervening. Recitation of ranges of values herein are merely intended to serve as a shorthand method of referring individually to each separate value falling within the range, unless otherwise indicated herein and each separate value is incorporated into the specification as if it were individually recited herein. The use of the term "set" (e.g., "a set of items") or "subset" unless otherwise noted or contradicted by context, is to be construed as a nonempty collection comprising one or more members. Further, unless otherwise noted or contradicted by context, the term "subset" of a corresponding set does not necessarily denote a proper subset of the corresponding set, but the subset and the corresponding set may be equal.

Operations of processes described herein can be performed in any suitable order unless otherwise indicated herein or otherwise clearly contradicted by context. Processes described herein (or variations and/or combinations thereof) may be performed under the control of one or more computer systems configured with executable instructions and may be implemented as code (e.g., executable instructions, one or more computer programs or one or more applications) executing collectively on one or more processors, by hardware or combinations thereof. The code may be stored on a computer-readable storage medium, for example, in the form of a computer program comprising a plurality of instructions executable by one or more processors. The computer-readable storage medium may be non-transitory.

Preferred embodiments of this disclosure are described herein, including the best mode known to the inventors for carrying out the invention. Variations of those preferred embodiments may become apparent to those of ordinary skill in the art upon reading the foregoing description. The inventors expect skilled artisans to employ such variations as appropriate and the inventors intend for embodiments of the present disclosure to be practiced otherwise than as specifically described herein. Accordingly, the scope of the present disclosure includes all modifications and equivalents of the subject matter recited in the claims appended hereto as permitted by applicable law. Moreover, any combination of the above-described elements in all possible variations thereof is encompassed by the scope of the present disclosure unless otherwise indicated herein or otherwise clearly contradicted by context.

All references, including publications, patent applications and patents, cited herein are hereby incorporated by reference to the same extent as if each reference were individually and specifically indicated to be incorporated by reference and were set forth in its entirety herein.

The invention claimed is:

1. A system for creating a customized electronic data sheet (EDS), the system comprising:
    at least one processor configured to execute program instructions to:
        in a configuration phase, receive layout instructions, through a graphical user interface (GUI), in connection with a customized page layout to be rendered for display in connection with entering and viewing clinical data of an EDS, wherein the customized page layout includes page objects, panel objects, and panel item objects that are nested within one another and relate to a specific medical procedure, and wherein the customized page layout provides for configuration of clinical data stored in a data source,
        in the configuration phase, build a nested EDS database structure for the customized page layout based on the layout instructions, wherein the nested EDS database structure defines a manner in which the customized page layout is rendered for display, in the configuration phase, receive a rule designation through the GUI, in the configuration phase, generate a rule, based on the rule designation, that binds clinical data stored in the data source to at least one of the page objects, panel objects or panel item objects of the customized page layout, the rule designating an operation to be automatically performed based on the clinical data, and in an implementation phase wherein user input selects the specific medical procedure for reporting, using the nested EDS database structure and the rule to render for display the custom page layout to enable the user to enter and view clinical data for the specific medical procedure.

2. The system of claim 1, wherein:

the rule involves at least one of a cross validation operation, a mathematical formula, a visibility decision, conditional formatting or a data filtering operation.

3. The system of claim 2, wherein:

the rule represents the cross validation operation and wherein the cross validation operation requires a second data value entered into a second panel field in response to a first data value being entered into a first panel field.

4. The system of claim 2, wherein:

the rule represents the visibility decision, in which at least one of a second panel or second panel field are either i) hidden and disenabled or ii) exposed and enabled in response to a first data value being entered into a first panel field.

5. The system of claim 1, wherein:

the rule represents a notification constraint that defines a constraint on a select data set, such that the processor is configured to perform a predefined action based on a change in the clinical data in the select data set.

6. The system of claim 5, wherein:

the predefined action includes at least one of validating the clinical data, filtering the clinical data, performing an automatic calculation based on the clinical data or confirming a user interface action based on the clinical data.

7. The system of claim 5, wherein:

in response to the change in the clinical data, the predefined action directs at least one of i) the panel to be hidden or ii) a control rule to enter an error state.

8. The system of claim 1, wherein:

the layout instructions define an arrangement, position, and format of a page, a panel within the page, and a panel field within the panel.

9. The system of claim 1, wherein:

the processor is further configured to define a linking rule that creates an association between the panel field and rules, wherein the linking rule defines an action in connection with conditions that occur relative to the panel field.

10. The system of claim 1, wherein:

the nested EDS database structure defines a nested page layout including a first panel within a first page, a first panel item within the first panel and wherein the first panel item further defines at least one of a second page or second panel that includes a second panel item.

11. A computer-implemented method for creating a customized electronic data sheet (EDS), the method comprising:

executing program instructions at one or more processors to:

in a configuration phase, receive layout instructions, through a graphical user interface (GUI), in connection with a customized page layout to be rendered for display in connection with entering and viewing clinical data of an EDS, wherein the customized page layout includes page objects, panel objects, and panel item objects that are nested within one another and relate to a specific medical procedure, and wherein the customized page layout provides for configuration of clinical data stored in a data source, in the configuration phase, build a nested EDS database structure for the customized page layout based on the layout instructions, wherein the nested EDS database structure defines a manner in which the customized page layout is rendered for display, in the configuration phase, receive a rule designation through the GUI, in the configuration phase, generate a rule, based on the rule designation, that binds clinical data stored in the data source to at least one of the page objects, panel objects or panel item objects of the customized page layout, the rule designating an operation to be automatically performed based on the clinical data, and in an implementation phase wherein user input selects the specific medical procedure for reporting, using the nested EDS database structure and the rule to render for display the custom page layout to enable the user to enter and view clinical data for the specific medical procedure.

12. The method of claim 11, wherein:

the rule involves at least one of a cross validation operation, a mathematical formula, a visibility decision, conditional formatting or a data filtering operation.

13. The method of claim 12, wherein:

the rule represents the cross validation operation and wherein the cross validation operation requires a second data value entered into a second panel field in response to a first data value being entered into a first panel field.

14. The method of claim 12, wherein:

the rule represents the visibility decision, in which at least one of a second panel or second panel field are either i) hidden and disenabled or ii) exposed and enabled in response to a first data value being entered into a first panel field.

15. The method of claim 11, wherein:

the rule represents a notification constraint that defines a constraint on a select data set, such that the processor is configured to perform a predefined action based on a change in the clinical data in the select data set.

16. The method of claim 15, wherein:

the predefined action includes at least one of validating the clinical data, filtering the clinical data, performing an automatic calculation based on the clinical data or confirming a user interface action based on the clinical data.

17. The method of claim 15, wherein:

in response to the change in the clinical data, the predefined action directs at least one of i) the panel to be hidden or ii) a control rule to enter an error state.

18. The method of claim 11, wherein:

the layout instructions define an arrangement, position, and format of a page, a panel within the page, and a panel field within the panel.

19. The method of claim 11, further comprising:

defining a linking rule that creates an association between the panel field and rules, wherein the linking rule defines an action in connection with conditions that occur relative to the panel field.

20. The method of claim 11, wherein:
the nested EDS database structure defines a nested page layout including a first panel within a first page, a first panel item within the first panel and wherein the first panel item further defines at least one of a second page or second panel that includes a second panel item.

\* \* \* \* \*